(12) United States Patent
Petyaev

(10) Patent No.: US 7,504,226 B2
(45) Date of Patent: Mar. 17, 2009

(54) METHODS RELATING TO TREATMENT OF ATHEROSCLEROSIS

(75) Inventor: Ivan Petyaev, Cambridge (GB)

(73) Assignee: Cambridge Theranostics Ltd., Cambridge (GB)

( * ) Notice: Subject to any disclaimer, the term of this patent is extended or adjusted under 35 U.S.C. 154(b) by 385 days.

(21) Appl. No.: 10/225,437

(22) Filed: Aug. 22, 2002

(65) Prior Publication Data

US 2003/0166029 A1 Sep. 4, 2003

Related U.S. Application Data

(60) Provisional application No. 60/323,127, filed on Sep. 18, 2001, provisional application No. 60/355,655, filed on Feb. 6, 2002.

(30) Foreign Application Priority Data

| Aug. 22, 2001 | (GB) | ................... | 0120428.8 |
| Feb. 6, 2002 | (GB) | ................... | 0202774.6 |
| Feb. 27, 2002 | (GB) | ................... | 0204611.8 |
| Jul. 16, 2002 | (GB) | ................... | 0216530.6 |
| Jul. 18, 2002 | (GB) | ................... | 0216755.9 |

(51) Int. Cl.
*G01N 33/92* (2006.01)

(52) U.S. Cl. ..................................... 435/7.2

(58) Field of Classification Search ............... None
See application file for complete search history.

(56) References Cited

U.S. PATENT DOCUMENTS

| 5,278,189 | A | 1/1994 | Rath et al. |
| 6,281,199 | B1 | 8/2001 | Gupta |
| 2004/0116350 | A1 | 6/2004 | Wentworth et al. |
| 2005/0129680 | A1 | 6/2005 | Wentworth et al. |

FOREIGN PATENT DOCUMENTS

| EP | 0561744 A1 | 9/1993 |
| EP | 0669132 A1 | 8/1995 |
| WO | 92/05780 A1 | 4/1992 |
| WO | 97/41227 | 11/1997 |
| WO | 98/57622 A1 | 12/1998 |
| WO | 01/22958 A2 | 4/2001 |
| WO | WO 02/22573 | 3/2002 |

OTHER PUBLICATIONS

Nevinsky et al., Biochemstry (Moscow) 65:1245-1255, 2000.*
(Cruse et al., Illustrated Dictionary of Immunol., 2nd ed., 2003, p. 42).*
Luo et al., Infect. Immun., 75:497-503, 2007.*
Colman, Res. Immunol., 145:33-36, 1994.*
Agil et al. (Clin. Chem., 41:220-225, 1995).*
Petyaev, Extraction of anti-lipoprotein abzymes from human atherosclerotic Lesion: Antibodies which bind and oxidise LDL, J Submicroscop Cytol Pathol, vol. 32, p. 477 (2000).
Kalayoglu et al, Cellular Oxidation of Low-Density Lipoprotein by *Chlamydia pneumoniae*, J Infect Disease, 1999, vol. 180, pp. 780-790.
Burian et al, Independent and Joint Effects of Antibodies to Human Heat-Shock Protein 60 and *Chlamydia pneumoniae* Infection in the Development of Coronary Atherosclerosis, Circulation, 2001, vol. 103, pp. 1503-1508.
Fong et al, Can an Antibiotic (Macrolide) Prevent *Chlamydia pneumoniae*-Induced Atherosclerosis in a Rabbit Model? Clinical Diagnostic Laboratory Immunology, 1999, vol. 6, No. 6, pp. 891-894.
Petyaev et al, Superoxide Dismutase Activity of Antibodies Purified from the Human Arteries and Atherosclerotic Lesions, Biochemical Society Transactions, Feb. 1998, vol. 26, No. 1, p. S43.
Sobal et al, Influence of Acetylsalicylic Acid on Oxidation of Native and Glycated Low-Density Lipoprotein, Life Sciences, Apr. 7, 2000, vol. 66, No. 20, pp. 1987-1998.
Steer et al, Aspirin protects low density lipoprotein from oxidative modification, Heart, 1997, vol. 77 No. 4, pp. 333-337.
Gurfinkel et al, Emerging role of antibiotics in atherosclerosis, American Heart Journal, Nov. 1999, vol. 138, No. 5, pp. S537-538.
Schwenke et al, Vitamin E Combined With Selenium Inhibits Atherosclerosis in Hypercholesterolemic Rabbits Independently of Effects on Plasma Cholesterol Concentrations, Circ. Res., Aug. 24, 1998, vol. 83, pp. 366-377.
Muhlestein et al, Infection With *Chlamydia pneumoniae* Accelerates the Development of Atherosclerosis and Treatment With Azithromycin Prevents It in a Rabbit Model, Circulation, vol. 97, pp. 633-636.
Wentworth et al, "Antibodies have the intrinsic capacity to destroy antigens", PNAS, Sep. 26, 2000, vol. 97, No. 20, pp. 10930-10935.

* cited by examiner

*Primary Examiner*—Robert B Mondesi
*Assistant Examiner*—Brian J Gangle
(74) *Attorney, Agent, or Firm*—Nixon & Vanderhye P.C.

(57) ABSTRACT

The present invention relates to the identification of lipid oxidising antibodies as a key pathogenic factor in atherosclerotic disorders. These disorders may be treated by inhibiting this antibody mediated lipid oxidation and methods and means for identifying and producing inhibitory agents are provided.

9 Claims, 13 Drawing Sheets

Figure 3

Interaction of ovine Chlamydia with anti-ApoB antibodies

Figure 13

METHODS RELATING TO TREATMENT OF ATHEROSCLEROSIS

This application claims the benefit of U.S. Provisional Application 60/323,127, filed on Sep. 18, 2001 and 60/355,655, filed on Feb. 6, 2002.

FIELD OF INVENTION

The present invention relates to methods for identifying and/or obtaining compounds useful in the treatment of atherosclerosis and related conditions in an individual.

BACKGROUND OF INVENTION

Auto-antibodies against such lipids as cholesterol [Swartz G. M., Jr., et al Proc. Natl. Acad. Sci. USA (1988), 85, 1902-1906, Alving C. R. and Swartz G. M., Jr. Critical Reviews in Immunology (1991), 10, 441-453.], phospholipids [Alving C. R. Biochem. Soc. Trans. (1984), 12, 342-344. ] and low density lipoproteins (LDL) are found in human plasma [Kabakov A. E. et al Clin. Immun. Immunopath. (1992), 63, 214-220, Mironova M et al Ibid. (1997), 85, 73-82. ] and are involved in the development of atherosclerosis [Lopes-Virella M. F. and Virella G. Clin. Immun. Immunopath. (1994), 73, 155-167, Kiener P. A. et al Arterioscler. Thromb. Vasc. Biol. (1995), 15, 990-999.].

Separately, neither antibodies nor LDL are a pathogenic factor, only the immune complex of the two [Tertov V. V et al Atherosclerosis (1990), 81, 183-189, Orekhov A. N. et al Biochem. Biophys. Res. Comm. (1989), 162, 206-211. ].

Immune complexes comprising unmodified plasma lipoproteins are known to have a low atherogenicity. However, if the lipoproteins become modified, in particular oxidised, these immune complexes become highly atherogenic [Orekhov A. N. et al Biobhem. Biophys. Res. Comm. (1989), 162, 206-211, Orekhov A. N. et al Arterioscler. Thromb. Vasc. Biol. (1991), 11, 316-326. ]. Oxidation of plasma lipids, which takes the form of peroxidation, is generally considered to be responsible for the development of atherosclerosis and is a consistently observed and published feature of this disease in the clinic [Goto Y. In: Lipid Peroxides in Biology and Medicine, Ed. Yagi K., Academic Press, New York, London, Tokyo (1982), 295-303, Halliwell B. and J. M. C. Gutteridge, Free Radicals in Biology and Medicine, Clarendon Press, Oxford, 1989, Schultz D et al Arterioscler. Thromb. Vasc. Biol. (2000), 20, 1412-1413. ]. However, until the present disclosure, the cause of this peroxidation in plasma was obscure.

SUMMARY OF INVENTION

The present invention relates to the discovery that a particular sub-group of auto-antibodies are capable of both binding and oxidising lipids and lipoproteins. These catalytic antibodies, which are the first reported example of anti-lipid abzymes, react with and oxidise low density lipoprotein to generate atherogenic factors, and they therefore represent a key pathogenic factor which is responsible for the development of atherosclerosis. Lipid-oxidising anti-self antibodies as described herein thus represent an important target for therapeutic intervention in the treatment of atherosclerosis-related conditions.

Aspects of the present invention relate to methods for identifying and/or obtaining agents which modulate the activity of lipid-oxidising anti-self antibodies (i.e. 'auto-antibodies') and which may for example, be useful in the treatment of atherosclerosis or other atherosclerotic disorder.

In general terms, an assay method for obtaining an inhibitor of antibody-mediated lipid peroxidation may comprise:
  (a) bringing into contact a lipid oxidising anti-self antibody and a test compound; and
  (b) determining binding of said test compound to said lipid oxidising anti self antibody.

BRIEF DESCRIPTION OF THE DRAWINGS

Figure 3:
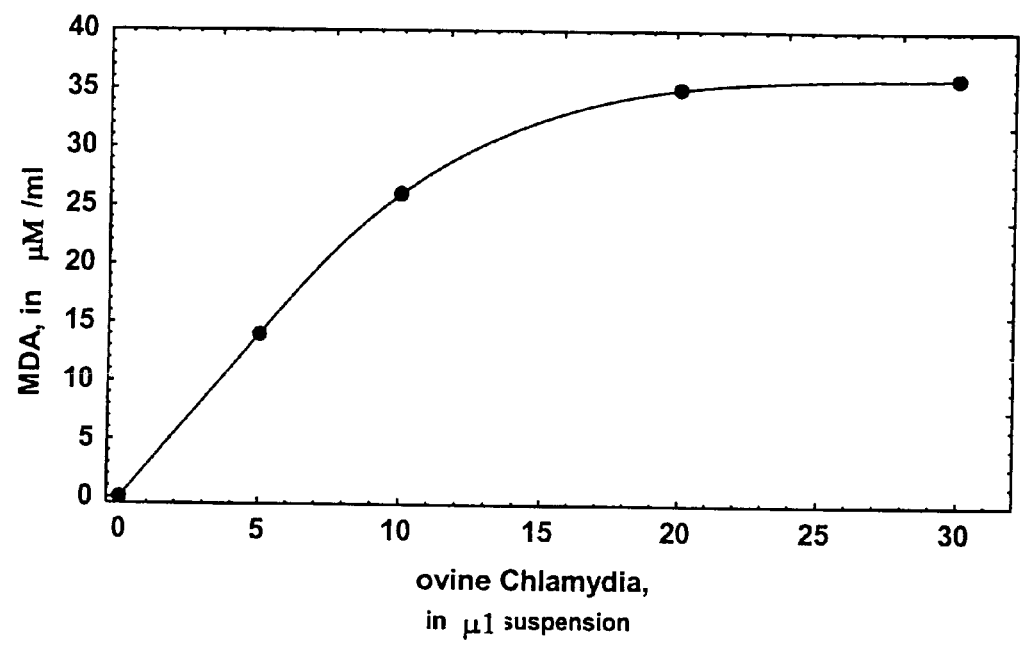

FIG. 3 shows the Michaelis-Menten kinetics of lipid peroxidation in ovine *Chlamydia* by 1.8:g human atherosclerotic lesion IgG; apparent $K_M$=13.3-16.1:1 of *Chlamydia* suspension; pH 5.7.

FIG. 13 shows the cross-reaction of anti-apolipoprotein B antibodies with *Chlamydia*.

DETAILED DESCRIPTION OF INVENTION

Figure 1:
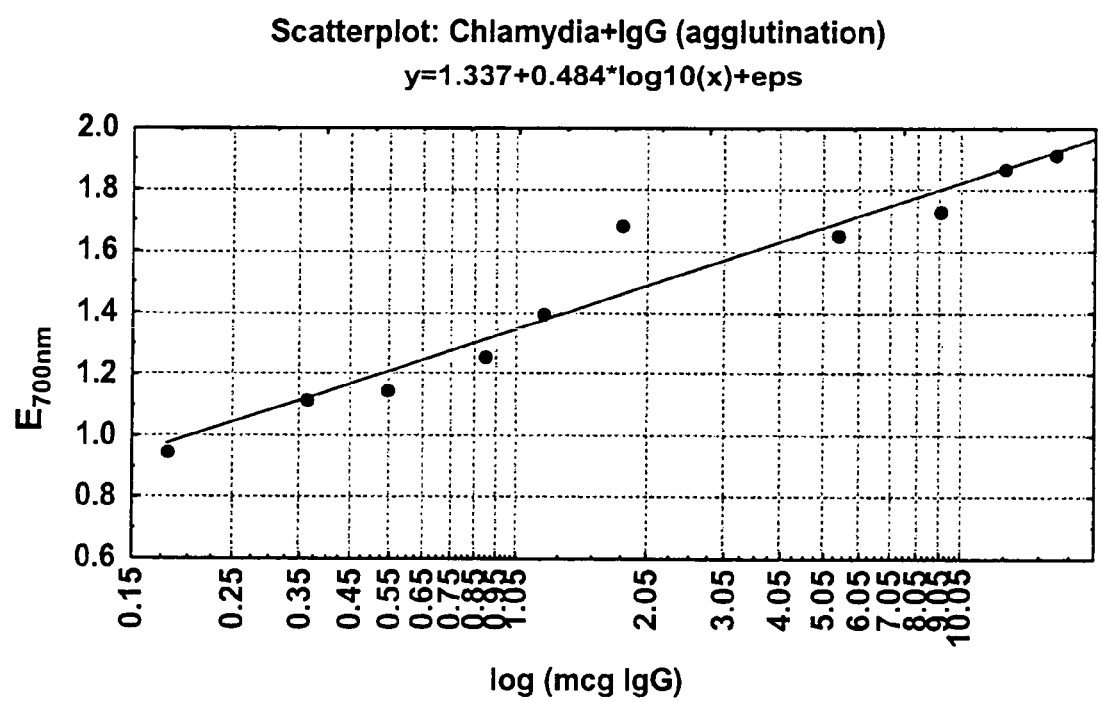
FIG. 1 shows the results of an agglutination reaction between 100:1 of ovine *Chlamydia* and IgG extracted from human atherosclerotic lesion.
Figure 2:
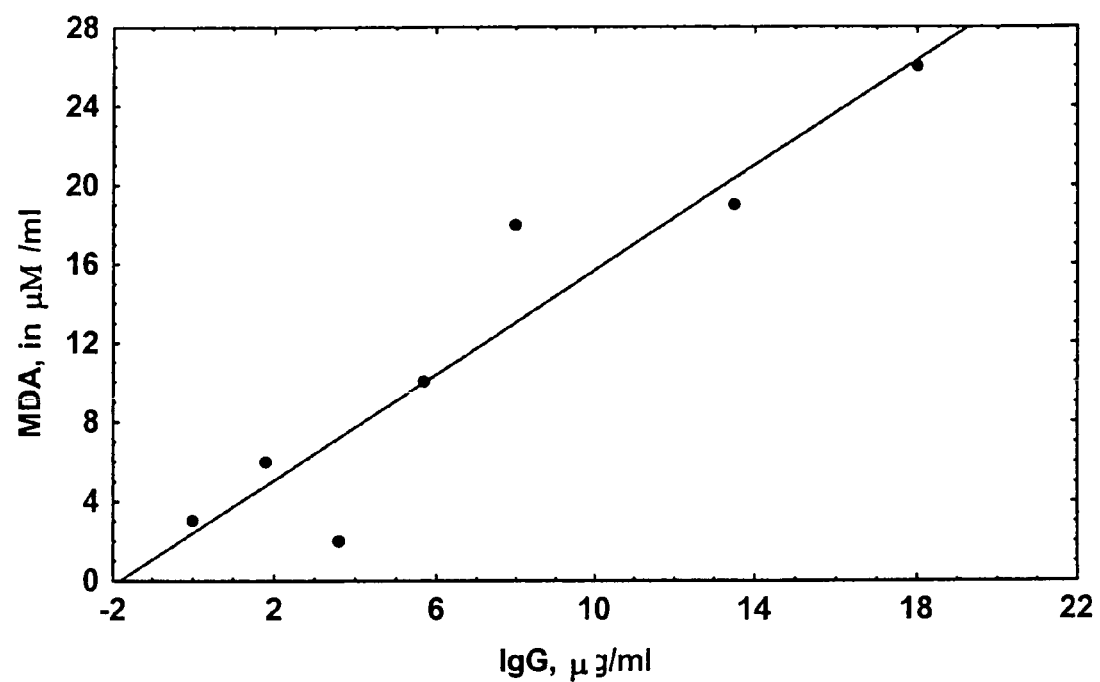
FIG. 2 shows the dependence of ovine *Chlamydia* peroxidation on the concentration of human atherosclerotic lesion IgG. Concentration of *Chlamydia* was constant and the pH was 5.7.

As described above, an assay method for obtaining an inhibitor of antibody-mediated lipid peroxidation may comprise in general terms:
  (a) bringing into contact a lipid oxidising anti-self antibody and a test compound; and (b) determining binding of said test compound to said lipid oxidising anti self antibody.

Binding between the test compound and the lipid oxidising antibody may be determined by any of a number of techniques available in the art, both qualitative and quantitative as described herein and is indicative of the test compound being a candidate modulator of antibody mediated lipid oxidisation. Determining binding may include measuring or detecting binding.

In some embodiments, a method may employ a sample from an individual and may comprise determining the binding of a lipid oxidising antibody to an antigen or the lipid oxidising activity of an antibody in the sample as described above in the presence of a test compound.

An assay method for obtaining an inhibitor of antibody-mediated lipid peroxidation may comprise:

(a) bringing into contact a lipid oxidising antibody and an antigen in the presence of a test compound; and, (b) determining binding of said antigen to said lipid oxidising antibody.

A method for screening for an inhibitor of antibody-mediated lipid oxidation may comprise:

(a) admixing a lipid oxidising antibody and an antigen in the presence of a test compound, said test compound being suspected of being an inhibitor of antibody-mediated lipid oxidation; and (b) determining any binding of said antigen to said lipid oxidising antibody in the presence of said test compound whereby said test compound is an inhibitor of antigen-mediated lipid oxidation when a lack of binding or decrease in binding of said antigen to said antibody in the presence of said test compounds is detected.

Such a method may be used to identify a test compound as an agent which modulates the binding and/or activity of a lipid oxidising antibody.

A suitable lipid-oxidising antibody may be obtained from a sample from an individual as described above, for example a sample from an atherosclerotic lesion of an individual. Alternatively, a lipid-oxidising antibody may be generated using conventional immunological means as described below. In some embodiments, an antibody may be isolated and/or purified.

A lipid oxidising antibody is a molecule which is a member of the immunoglobulin super-family that is associated with both binding and catalytic activity. After purification, for example, using protein G, a lipid oxidising antibody displays both binding to antigen and catalytic activity (i.e. lipid oxidation). The lipid oxidising antibody may be an anti-self antibody i.e. the antibody may bind specifically to an antigen from the individual or host which produced the antibody.

Binding of the lipid oxidising antibody with the antigen in the presence of a test compound may be compared with the interaction of the lipid oxidising antibody to the antigen in comparable reaction medium and conditions in the absence of a test compound.

A difference (i.e. an increase or decrease) in binding in the presence of test compound relative to the absence is indicative that the test compound is an agent which is able to modulate the binding of lipid oxidising antibody and antigen.

Test compounds which reduce or inhibit the binding of a lipid oxidising antibody and an antigen may be identified using conditions which, in the absence of a positively-testing agent, allow such binding to occur. Such compounds may be used as agents to inhibit the function of lipid oxidising abzymes, for example in the treatment of atherosclerotic disorders.

A difference (i.e. an increase or decrease) in binding in the presence of test compound relative to the absence is indicative that the test compound is an agent which is able to modulate the binding of lipid oxidising antibody and antigen.

An suitable antigen may be a lipid antigen, for example a lipid, lipoprotein or lipopolysaccaride as further described below.

An assay method of the invention may further comprise determining the oxidising activity of the antibody.

An assay method for obtaining a inhibitor of a lipid oxidising antibody may comprise:

(a) bringing into contact a lipid oxidising antibody and a test compound; and, (b) determining lipid oxidation activity of said lipid oxidising antibody.

The lipid oxidising antibody and the test compound may be brought together in the presence of a lipid antigen. Lipid oxidising activity may be determined by determining the oxidation of the lipid antigen by the lipid oxidising antibody i.e. the lipid oxidation activity of said antibody may be inferred from measurement of the oxidation of the lipid antigen.

Lipid oxidising activity in the presence of a test compound may be compared with lipid oxidising activity in comparable reaction medium and conditions in the absence of a test compound. A difference (i.e. an increase or decrease) in lipid oxidising activity in the presence of test compound relative to the absence is indicative that the test compound is an agent which is able to modulate the activity of a lipid oxidising antibody.

Test compounds which reduce or inhibit the activity of a lipid oxidising antibody may be identified using conditions in which, in the absence of a positively-testing agent, the antibody oxidises lipid. Such compounds may be used as agents to inhibit the function of lipid oxidising abzymes, for example in the treatment of atherosclerotic disorders.

A method for screening for an inhibitor of antibody-mediated lipid oxidation may comprise:

(a) admixing a lipid oxidising antibody and a lipid antigen in the presence of a test compound, said test compound being suspected of being an inhibitor of antibody-mediated lipid oxidation; and (b) determining oxidation of said lipid antigen to said lipid oxidising antibody in the presence of said test compound whereby said test compound is an inhibitor of antigen-mediated lipid oxidation when a lack of oxidation or decrease in oxidation of said antigen in the presence of said test compound is detected.

Such a method may be used to identify a test compound as an agent which modulates the binding and/or activity of a lipid oxidising antibody.

The determination of binding or activity may be quantitative or qualitative and may include detecting the existence of the binding or activity, which may, for example, include detecting the existence of a binding or activity above a certain threshold value, and measuring the amount or level of the binding or activity.

A method may, for example, comprise capturing an antibody from a serum sample, for example using an immobilised anti-idiotypic antibody, and determining the lipid oxidation activity of the captured antibody in the presence and absence of test compound.

An antigen may be a member of a family of molecules sharing high sequence identity (i.e. homologues) which are found in a range of infectious agents (for example, in two or more species of gram -ve bacteria) or the antigen may be specific to a particular infectious agent (i.e. it does not have homologues in other species). Moreover, the same epitope may be present in antigens from different infectious agents which do not otherwise share high levels of sequence identity (i.e. non-homologues). Examples of antigens which are common to a range of infectious agents include apo-lipoprotein B, OmpA, lipopolysaccharide, hsp60 MQMP, (P)OMP, p54 and lipid A.

Both binding and catalytic activities may be intrinsic to a lipid oxidising antibody. Alternatively, the lipid oxidising activity may be due to a catalytic molecule which is tightly bound to the antibody and co-purifies with it (for example, using a Protein G/Protein A or Protein L column) in a complex. This catalytic molecule may be an immunoglobulin or a non-immunoglobulin, such as an enzyme or a metal ion. After purification, the complex displays binding activity from the antibody and catalytic activity from the catalytic molecule. A lipid oxidising antibody may, alternatively, initiate lipid oxidation by another mechanism e.g. by altering the lipid antigen environment (e.g. via the activation of monocytes) or altering the lipid or lipoprotein to facilitate oxidation of lipid.

A catalytic antibody may be specific for a particular epitope which is carried by a number of antigens and may therefore bind to different antigens which carrying the same epitope. The antibody may show no significant binding to other epitopes. The antibody is thus said to 'bind specifically' to the epitope or to an antigen comprising the epitope. An epitope which is recognised by the antibody may be shared by a host molecule and an antigen from an infectious agent, for example a bacterium, fungus, virus or protozoa. A lipid oxidising antibody produced by a host in response to a foreign antigen, for example during pathogenic infection, may thus cross-react with host lipids or lipoproteins or other antigens.

The lipid oxidising antibody may thus bind to both a host antigen (i.e. an anti-self antibody) and a foreign antigen and may catalyse the oxidation of one or both of these molecules.

An antibody in a method as described herein may be isolated, purified and/or extracted from a sample, it may be comprised within a serum, plasma, blood or other biological sample, or it may comprised within the vascular system of an animal model. Preferably the antibody is in a blood, serum or plasma sample. An antibody or antibody molecule as described herein may, for example, be an IgG molecule from said sample.

Individuals from whom samples are taken and/or in whom abzyme activity is modulated, may include humans and non-human animals, including domestic animals such as dogs, cats, horses and parrots, farm animals such as sheep and cattle and rare or exotic animals such as elephants and tigers. References to 'human' herein should be understood to include 'non-human animal' except where the specific context dictates otherwise.

Antibody molecules which catalyse the oxidation of lipid are referred to herein as catalytic antibody molecules, anti-lipid abzymes, abzymes or lipid oxidising antibodies. As described above, such catalytic antibodies may have an intrinsic or inherent lipid oxidase activity or other activity which leads to lipid oxidation or may be naturally associated (i.e. bound or attached in a non-covalent manner in their natural state within the body) with a molecule having lipid oxidase activity.

Lipid oxidising antibodies may be isolated from an atherosclerotic lesion of an individual suffering from an atherosclerotic disorder. Alternatively, lipid-oxidising anti-self antibody may be obtained using conventional immunological techniques.

Methods of producing such antibodies include immunising a mammal (e.g. mouse, rat, rabbit, horse, goat, sheep or monkey) with an antigen, which may, for example, be a Chlamydial cell antigen. Antibody molecules may be obtained from immunised animals using any of a variety of techniques known in the art, and screened, for example using lipid oxidation assays as described herein and/or determining binding of antibody to the antigen of interest. Western blotting techniques or immunoprecipitation may be used (Armitage et al. 1992, Nature 357: 80-82). Isolation of antibodies and/or antibody-producing cells from an animal may be accompanied by a step of sacrificing the animal.

Another approach is to identify suitable lipid oxidising antibodies by screening phage display libraries using standard techniques (See Chapter 18 Sambrook et al, Molecular Cloning: A Laboratory Manual Revised Edition, Cold Spring Harbor Lab Press (31, Dec. 2000), Dematis et al J. Mol. Biol. (1999) 286(2) 617-633, Harrison et al Methods Enzymol. (1996) 267 83-109).

The experimental data herein shows that a sub-group of the antibodies which are raised in response to *Chlamydia* infection are auto-antibodies which cross react with host antigen and cause plasma lipid peroxidation. Catalytic anti-*Chlamydia* antibodies are shown to be present in anti-lipoprotein IgG fractions extracted from human atherosclerotic lesions and the sera of patients with clinical complications of atherosclerosis, but absent from IgG extracted from the sera of healthy people. Catalytic antibodies which bind and oxidise lipid as described herein may therefore be reactive with i.e. bind to, a *Chlamydia* cell.

Whilst atherosclerosis has been linked in the past to the presence in the arterial wall of the bacteria *Chlamydia pneumoniae* [Roivainen M. et al Circulation (2000), 101, 252-257, Siscovick D. S. et al. J. Infect. Dis. (2000), 181, Suppl. 3, S417-420], a serological test to detect specific anti-*Chlamydia* antibodies in the plasma or serum of patients [Mendall M. et al (1995) J. Infect. 30 121-128, Wang S-P et al (1970) 70 367-374] cannot be used to identify or distinguish a patient with atherosclerosis. A significant part of the population have a history of *Chlamydia* infection and, as result of this, have specific anti-*Chlamydia* antibodies in their sera, without any clinical manifestation of atherosclerosis [Davidson M. et al Circulation (1998), 98, 628-633m, Song Y. G. et al Yonsei Med. J.(2000), 41, 319-327. ]. Anti-*Chlamydia* antibodies per se in the plasma or serum are not therefore indicative of atherosclerosis and are not potential targets for therapy.

However, catalytic anti-*Chlamydia* antibodies which cross-react with human antigens and catalyse the oxidation of plasma lipoproteins are shown herein to be useful as targets for the treatment of atherosclerotic disorders.

Lipid oxidising antibody molecules may thus be anti-*Chlamydia* abzymes or antibody molecules i.e. they bind or are reactive with a *Chlamydia* cell antigen.

A *Chlamydia* antigen as described herein may be any immunogen or immunogenic component of a *Chlamydia* cell i.e. a molecule from *Chlamydia* which evokes or is capable of evoking an immune response in a mammal against the *Chlamydia* cell, for example Hsp60 (Huittinen et al (2001) Eur Resp. J. 17(6) 1078-1082, Kinnunen A. et al (2001) Scand. J. Immunol. 54(1-2) 76-81). Preferably, the antigen is a protein or lipid antigen i.e. it comprises or consists of a lipid group or moiety. A lipid antigen may be, for example, a lipid, lipoprotein or other lipid associated cell component which binds anti-*Chlamydia* antibodies and the term 'lipid antigen' refers to any of these components. Such an antigen may be purified and/or isolated or comprised within a *Chlamydia* cell. Antibodies raised against human apo-lipoprotein B have been shown to be reactive with Chlamydial cells (see Example 7). In some embodiments, a lipid oxidising antibody as described herein may be reactive with human apolipoprotein B.

Suitable methods for purifying and/or isolating such a lipoprotein are well known in the art, and include, for example, HPLC.

A Chlamydial cell may be a cell from a species belonging to the *Chlamydia psittaci* group. The *Chlamydia psittaci* group includes *Chlamydia psittaci* and *Chlamydia pneumoniae*. In some preferred embodiments, the Chlamydial cell is an ovine *Chlamydia psittaci* cell. Suitable preparations of live ovine *Chlamydia psittaci* in a lyophilised form are available commercially (Intervet).

Assay methods for modulators of antibody mediated lipid oxidation, as described herein, are particularly suited to high throughput formats. Such formats are well known for use in large scale automated screening programs.

A test compound which is a candidate inhibitor may be a small chemical entity, peptide, antibody molecule or other molecule whose effect on the lipid oxidising activity or binding between a lipid oxidising antibody and a lipid antigen is to be determined. Suitable test compounds may be selected from compound collections and designed compounds, for example using combinatorial chemistry as described below. Particular suitable test compounds include metal chelators, antioxidants, epitope mimics and anti-idiotypic antibodies as described herein.

Combinatorial library technology (Schultz, J S (1996) Biotechnol. Prog. 12:729-743) provides an efficient way of testing a potentially vast number of different substances for ability to modulate the activity of a lipid oxidising antibody. As described above, prior to or as well as being screened for modulation of lipid oxidising activity, test substances may be screened for ability to bind with the antibody. This may be used as a coarse screen prior to testing a substance for actual ability to modulate activity of the antibody.

The amount of test substance or compound which may be added to an assay of the invention will normally be determined by trial and error depending upon the type of compound used. Typically, from about 0.01 to 100 nM concentrations of putative inhibitor compound may be used, for example from 0.1 to 10 nM.

Compounds which may be used may be natural or synthetic chemical compounds used in drug screening programmes. Extracts of plants which contain several characterised or uncharacterised components may also be used.

Other candidate inhibitor compounds may be based on modelling the 3-dimensional structure of the lipid oxidising antibody and/or the lipid antigen to which it binds and using rational drug design to provide potential inhibitor compounds with particular molecular shape, size and charge characteristics.

The reactivity and catalytic activity of an antibody molecule may be determined by any appropriate means. In some embodiments, an antibody molecule, an anti-idiotypic antibody which binds to the antibody molecule, or a *Chlamydia* cell or antigen may be tagged with an individual reporter molecule. In other embodiments, a reporter molecule or substance may be encapsulated in a liposome or other microcontainer and released in the medium for detection when the liposome is degraded by lipid oxidation. The reporter molecules may directly or indirectly generate detectable, and preferably measurable, signals.

Where required, linkage of reporter molecules may be direct or indirect, covalent, e.g. via a peptide bond, or non-covalent. Linkage via a peptide bond may be as a result of recombinant expression of a gene fusion encoding binding molecule (e.g. antibody) and reporter molecule.

One mode is by covalent linkage of each binding member with an individual fluorochrome, phosphor or laser dye with spectrally isolated absorption or emission characteristics. In other formats, fluorochromes or dyes may be encapsulated in liposomes. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples are horseradish peroxidase and chemiluminescence. Any such method may be used to determine the binding of an antibody to an antigen, particularly a lipid or *Chlamydia* antigen, or the lipid oxidation activity. One or more of these may be determined, for example, in the presence of a test compound.

The mode of determining binding is not a feature of the present invention and those skilled in the art are able to choose a suitable mode according to their preference and general knowledge.

Lipid oxidation activity, including lipid peroxidation activity, may be determined by determining the oxidation of host lipid (i.e. lipid from the sample), lipid from a foreign antigen such as a *Chlamydia* cell, or lipid from another source, which may for example be added as part of an assay method.

Lipid oxidation may be determined by measuring the accumulation of products or by-products, such as co-oxidised coupled reporter molecules or the disappearance or consumption of substrates such as non-modified lipids or co-substrates such as oxygen.

Many methods for determining lipid peroxidation are known in the art and are suitable for use in accordance with the present invention. The precise mode of determining lipid oxidation is not a feature of the present invention and those skilled in the art are able to choose a suitable mode according to their preference and general knowledge.

Suitable methods are, for example, described in CRC Handbook of Methods for Oxygen Radical Research, CRC Press, Boca Raton, Fla. (1985), Oxygen Radicals in Biological Systems. Methods in Enzymology, v. 186, Academic Press, London (1990); Oxygen Radicals in Biological Systems. Methods in Enzymology, v. 234, Academic Press, San Diego, New York, Boston, London (1994); and Free Radicals. A practical approach. IRL Press, Oxford, New York, Tokyo (1996)

In preferred embodiments, oxidation is determined by determining the production (i.e. the presence or amount) of a lipid oxidation product.

Oxidation products and/or intermediates of the lipids in which oxidation was initiated may be determined or oxidation products and/or intermediates may be determined of lipids in which oxidation is propagated.

A suitable lipid oxidation product may include aldehydes such as malondialdehyde (MDA), (lipid) peroxides, diene conjugates or hydrocarbon gases. Lipid oxidation products may be determined by any suitable method. For example, lipid peroxidation products may be determined using HPLC (Brown, R. K., and Kelly, F. J In: Free Radicals. A practical approach. IRL Press, Oxford, New York, Tokyo (1996), 119-131), UV spectroscopy (Kinter, M. Quantitative analysis of 4-hydroxy-2-nonenal. Ibid., 133-145), or gas chromatography-mass spectrometry (Morrow, J. D., and Roberts, L. J. $F_2$-Isoprostanes: prostaglandin-like products of lipid peroxidation. Ibid., 147-157).

The peroxidation of lipid may lead to an oxidation of proteins, carbohydrates, nucleic acids and other types of molecules. The products of such oxidation can also be used for indirect measurement of the activity of the abzymes. In addition, peroxidation may lead to changes in the properties of reporter molecules associated with propagating lipid oxidation. As described below, reporter molecules may be encapsulated in these lipids, for example as liposomes, and release of the reporter molecule from the liposome is indicative of oxidation.

Suitable reporter substances and molecules may include intact luminous bacteria, luminol, lucigenin, pholasin and luciferin. Such substances may, for example, be coupled to $H_2O_2/O_2$.—$/O_2$— utilizing molecules such as peroxidase, esterase, oxidase, luciferase, catalase, superoxide dismutase, perylene, $NAD^+$, and acridinium esters bis (trichlorophenyl) oxalate (Campbell A. K. Chemiluminescence. VCH, Ellis Horwood Ltd., England, 1988)

Other materials susceptible to free radical chain reactions may also be used to determine lipid oxidation. For example, lipid peroxidation, as a chain process, initiates and enhances the polymerisation of acrylamide. Lipid oxidation may thus be determined by the determining the co-polymerisation of $^{14}$C-acrylamide (Kozlov Yu P. (1968) Role of Free Radicals in normal and pathological processes. Doctorate thesis—MGU Moscow 1968)

Since lipid and lipoprotein peroxidation is a free radical mediated process, lipid oxidising abzymes may be measured by detection of these radicals. Radicals may be detected or determined using intrinsic low-level chemiluminescence (with or without sensitisors) (Vladimirov, Y. A., and Archakov, A. I. Lipid Peroxidation in Biological Membranes. Nauka, Moscow (1972); Vladimirov, Y. A. Intrinsic low-level chemiluminescence. In: Free Radicals. A practical approach. IRL Press, Oxford, New York, Tokyo (1996), 65-82)., electron spin resonance (with spin trapping (Mason, R. P. In vitro and in vivo detection of free radical metabolites with electron spin resonance. In: Free Radicals. A practical approach. IRL Press, Oxford, New York, Tokyo (1996), 11-24) or without spin trapping (Petyaev, M. M. Biophysical approaches in the diagnosis of cancer. Medicina, Moscow (1972)) or other techniques well known in the art. Lipid oxidation may also be determined by determining the consumption of fatty acids or other substrates of this reaction.

In some preferred embodiments, the production of malondialdehyde (MDA) is determined, following reaction with 2-thiobarbituric acid (conveniently at 1 mM) by measuring absorbance at an appropriate wavelength, for example 525 nm.

Lipid which is oxidised by an anti-*Chlamydia* abzyme may include the lipid moiety of a lipoprotein, fatty acid, phospholipid, cholesterol, cholesterol ester or triglyceride.

As described above, the lipid oxidation activity of an abzyme may also lead to the oxidization of protein, carbohydrate and/or nucleic acid, for example the protein and/or carbohydrate moieties of a lipoprotein.

Chlamydial lipid oxidation is determined in some preferred embodiments because it provides for a convenient one step assay, which may be used to determine, for example, the presence or absence of an anti-*Chlamydia* abzyme. Oxidation of Chlamydial lipid will occur when a *Chlamydia*-specific antibody is present which binds and oxidises *Chlamydial* antigen comprising a lipid.

In methods according to these preferred embodiments, an antigen may be a Chlamydial cell antigen.

A method for obtaining a modulator of the activity of a lipid oxidising antibody may include;

i) contacting a lipid oxidising antibody and a Chlamydial cell antigen in the presence of a test compound; and ii) determining the lipid oxidation activity of lipid oxidising antibody.

In some embodiments, a method may include:

determining the lipid oxidation activity of an antibody molecule from a sample obtained from the individual in the presence of a test compound, wherein said antibody molecule binds to a *Chlamydia* antigen.

In other embodiments, a method may include:

determining the binding to a *Chlamydia* antigen of an antibody molecule from a sample obtained from the individual in the presence of a test compound, wherein said antibody molecule possesses lipid oxidation activity (i.e. oxidises lipids).

In still further embodiments, a method may include:

determining the binding to a *Chlamydia* antigen of an antibody molecule from a sample obtained from an individual in the presence of a test compound; and, determining the lipid oxidation activity of said antibody molecule.

Determining the oxidation of the lipid may include determining the amount, level or degree of oxidation which is induced by contact with the *Chlamydia* antigen. Preferably, the Chlamydial cell antigen is a lipid antigen and the oxidation of the lipid antigen is determined.

An antigen may be purified and/or isolated or, more preferably, it may be comprised within an intact membrane, for example on the surface of a *Chlamydia* cell.

The oxidation of lipid, for example in a sample, in the presence of the *Chlamydia* cell or antigen may be compared with the oxidation of lipid in the absence of the *Chlamydia* cell or antigen. An increase in lipid oxidation is indicative of the presence of an anti-lipid abzyme.

A method for identifying and/or obtaining a modulator of the activity of a lipid oxidising antibody may include i) contacting a lipid oxidising antibody with a *Chlamydia* cell in the presence of a test compound; and ii) determining the oxidation of the lipid of said cell.

An increase in *Chlamydia*-dependent lipid oxidation in the presence relative to the absence of a test compound is indicative of the test compound being an inhibitor of anti-lipid abzyme.

Lipid/lipoprotein peroxidation is a free radical chain reaction and is capable of self-propagation from one molecule to another, to a lipid-contained micelle, or to a whole cell (after attaching to its membrane via receptors or non-specific absorption) (Chemical and Biochemical Aspects of Superoxide and Superoxide Dismutase. Elsevier/North-Holland, New York, Amsterdam (1980); Lipid Peroxides in Biology and Medicine. Academic Press, Orlando, San Diego, San Francisco, New York, London (1982); Halliwell, B., and Gutteridge, J. M. C. Free Radicals in Biology and Medicine. Clarendon Press. Oxford (1996); Oxidants, Antioxidants, and Free Radicals. Taylor and Francis, Washington (1997)).

In some embodiments of the methods described herein, the propagation of peroxidation is used to determine the activity of lipid-oxidising abzymes.

For example, a microcontainer such as a liposome, vesicle or microcapsule which has a membrane which made of a material susceptible to free radical decomposition, for example a phospholipid membrane, may be loaded with a dye, fluorochrome or other reporter substance or detecting material, for example: Eosin, Fluorescamine, Rhodamine B or Malachite Green, and used in the detection of a lipid oxidising abzyme. Lipid oxidation in the methods described herein may thus be determined by determining the release of the encapsulated reporter substance.

The loaded microcontainer may be mixed with a sample of plasma or serum. A *Chlamydia* antigen, conveniently comprised in or part of a *Chlamydia* cell, is then added to the mixture. Any lipid oxidising abzymes in the sample then bind to the antigen and initiate peroxidation.

Initiation of the lipid/lipoprotein oxidation by the interaction of *Chlamydia* antigen with an abzyme will self propagate and spread to the coating of the microcontainer. This damages the coating and causes the release of the reporter substance into the surrounding solution. This release is then detected.

For example, a loaded microcontainer may be contacted with an anti-lipid abzyme in the presence of a test compound. A *Chlamydia* antigen, conveniently comprised in or part of a *Chlamydia* cell, is then added. In the absence of the test compound being an inhibitor of a lipid oxidising abzyme, the abzyme binds to the antigen and initiates peroxidation. Release of the reporter substance therefore occurs as a result of contacting said antibody with the microcontainer or a composition comprising said reporter substance in said microcontainer.

An assay method may include;
  i) contacting a lipid oxidising antibody with a Chlamydial cell antigen and a test compound in the presence of a microcontainer susceptible to lipid oxidation and containing a reporter substance; and
  ii) determining the release of said reporter substance from the microcontainer.

If the intensity of the signal produced by the release of the reporter is not sufficient to cause a registerable or detectable signal, a free radical propagator or sensitiser can be included in the reaction mixture, for example: free ions and complexes of $Fe^{2+}/Co^{2+}$ or other metals of transient valence. These and other sensitisers serve to multiply the amount of free radicals in a system.

Release of incorporated material from the microcontainer leads to changes in the physical/chemical properties of the reaction mixture which can be registered visually (or by other conventional means). Alternatively, damaged/fragmented/dissolved microcontainers can be separated from unmodified ones either by active centrifugation or by passive sedimentation.

Instead of liposomes or other microcontainers (loaded with reporter substances), erythrocytes from the blood sample itself may be used as a target for the propagating lipid/lipoprotein peroxidation caused by anti-lipid abzymes. *Chlamydia* bacteria or antigens may be introduced or contacted with a blood sample, optionally in the presence of a sensitiser to ensure propagation of the peroxidation reaction. Lipid oxidation may be determined by determining the haemolysis of erythrocytes in the blood sample. This may be performed in the presence of a test compound.

Any initiation of the lipid/lipoprotein oxidation by the interaction of *Chlamydia* antigen with abzyme in the sample will self propagate and spread to the erythrocyte cell membrane, leading to damage and eventually cell lysis. Thus, haemolysis occurs as a result of contacting said antibody with a lipid with a composition comprising erythrocytes. The appearance of haemolysis in the sample of the whole blood in response to the addition of *Chlamydia* bacteria/antigens is therefore indicative of the presence of lipid oxidising abzymes. Haemolysis may be determined by any suitable method.

A method may include;

i) contacting a lipid oxidising antibody, a Chlamydial cell antigen and a test compound in the presence of erythrocytes; and ii) determining the haemolysis of said erythrocytes.

As described above, an assay method may be performed in the presence and absence of test compound. A difference in the amount of haemolysis in the presence, relative to the absence of test compound is indicative of the test compound being an inhibitor of antibody-mediated lipid oxidation.

These embodiments may be preferred in some circumstances because samples do not require a separation of plasma/serum from the erythrocytes prior to their analysis. Liposomes or other microcontainers may be loaded with, for example, a material which can develop a colour different to the red colour of haemoglobin. Alternatively, spinning of the tested samples or even passive sedimentation would separate undamaged microcontainers/erythrocyte. Release of reporter dye or haemolysis is indicative of the presence of lipid-oxidising antibodies in the analysed material. The intensity of the signal correlates with their activity/concentration.

Since whole blood may be analysed using the methods described above, these methods do not involve a centrifugation step and may be used in non-laboratory or domestic conditions. The presence or severity of atherosclerosis may, for example, be determined by comparing the observed reporter signal or haemolysis with known values in atherosclerosis patients and normal individuals. Such a comparison may be carried out using a chart, scale, graph or calibration which indicates the amount or level of reporter signal or haemolysis at particular stages or severities of atherosclerosis.

Lipid peroxidation is a redox process which may also be measured using a coupled redox system. Suitable redox systems include physical and chemical systems. For example a sensor chip may be used to detect changes in the redox potential of a lipid oxidation reaction coupled thereto. A range of sensor chips based either on redox enzymes or on redox mediators are known in the art. Both of these types of sensors can be adjusted/used for the detection of free radical molecules or redox molecules coupled with them (Hall E. A. H. Biosensors. Redwood Press Ltd., Great Britain, 1990).

Accumulation of $H_2O_2$ produced by lipid peroxidation may be measured, for example, by addition of the coupled peroxidase-based reaction which will use hydrogen peroxide to oxidise its other co-substrate(s) and produce a coloured product. An accumulation of $O_2^{\bullet}$ produced by lipid peroxidation can be determined by using $O_2^{\bullet-}$-sensitive molecules, such as cytochrome C or riboflavin.

Alternatively, lipid peroxidation consumes molecular oxygen, hence any $O_2$-dependent chemical reaction or physical process can be used, for example, oxygen electrode or polarography. (Polarography. Ed. Kolthoff I. M., Lingane J. J. Interscience Publishers, New York, London, 19520).

Methods according to some aspects of the present invention may include obtaining a sample of blood, serum or plasma from an individual. A test sample of serum or plasma may be obtained, for example, by extracting blood from an individual and isolating the serum or plasma from the extracted blood. Suitable extraction methods include centrifugation to separate serum and plasma from cellular material.

Methods of the present invention may be performed in vitro using samples obtained from an individual or on antibodies isolated therefrom, or may be performed in vivo using an animal model system as described herein. An in vivo method employing an animal model system may comprise the step of sacrificing the animal.

In using methods of the present invention, the skilled person is well aware of the need to employ appropriate control experiments.

An atherosclerotic disorder as described herein may include atherosclerosis, ischaemic (coronary) heart disease: myocardial ischaemia(angina), myocardial infarction; aneurismal disease; atheromatous peripheral vascular disease: aortoiliac disease, chronic and critical lower limb ischaemia, visceral ischaemia, renal artery disease, cerebrovascular disease, stroke, atherosclerotic retinopathy, thrombosis and aberrant blood clotting and hypertension. Such conditions may be medical or veterinary conditions.

The conditions described above are closely related and a predisposition to one such condition may be indicative of a predisposition to other such conditions.

An agent identified using one or more primary screens (e.g. in a cell-free system) as having ability to modulate the binding of antibody to a lipid antigen and/or the lipid oxidising activity of the antibody may be assessed further using one or more secondary screens. A secondary screen may involve testing for lipid oxidising antibody levels in the vascular system or a biological function of a lipid oxidising antibody, for example, in an animal model as described below.

Suitable biological functions which may be assessed in a secondary screen include reduction in size or number of atherosclerotic lesions, or a reduction in other symptoms or effects of an atherosclerotic disorder, such as blood pressure.

Methods of the present invention may include identifying a test compound as an agent which modulates the binding and/or activity of a lipid oxidising antibody.

Assay methods may include isolating, purifying and/or manufacturing a compound identified as a modulator of lipid oxidising antibody binding and/or activity.

Optionally, compounds identified as agents which modulate the binding and/or activity of a lipid oxidising antibody using an assay method described herein may be modified to optimise activity or provide other beneficial characteristics such as increased half-life or reduced side effects upon administration to an individual.

Assay methods of the present invention may further include formulating the agent into a composition, such as a medicament, pharmaceutical composition or drug, with a pharmaceutically acceptable excipient as described below. Such a composition may be administered to an individual.

The precise format of assay methods of the invention may be varied by those of skill in the art using routine skill and knowledge.

An animal model of atherosclerotic disorders is useful in order to follow the progression of disease caused by lipid oxidising antibodies and determine various disease parameters such as rate of clearance. A model is also useful in testing compounds as potential therapeutics for the reduction of abzyme levels and concomitant improvement in symptoms. An animal model may be used instead of an in vitro screen or may form a secondary screen. For example, candidate lead compounds identified in an in vitro drug screen may be tested in the animal model before progressing to clinical trials.

Another aspect of the invention provides a method of generating a animal model for an atherosclerotic condition comprising introducing one or more *Chlamydia* cell antigens into the vascular system of a non-human animal, thereby generating said animal model.

The production of lipid oxidising antibodies reactive with said one or more *Chlamydia* antigens may be determined in the vascular system of said animal following said introduction.

A *Chlamydia* cell antigen may be comprised within or on the surface on a *Chlamydia* cell. *Chlamydia* cells may include cells of *Chlamydia* strains which do not naturally infect the non-human mammal, for example human *Chlamydia* pathogens such as *C. pneumoniae*.

Chlamydial antigens or cells may be introduced by any known method of inoculation into the vascular system of the non-human mammal.

Suitable non-human animals include mammals such as rabbits, sheep, goats, mice, rats, guinea pigs, camels and pigs.

Other aspects of the invention relate to animal models for atherosclerotic conditions produced by these methods.

An animal model for an atherosclerotic condition may comprise a non-human animal having lipid oxidising antibodies in the vascular system thereof, wherein said lipid oxidising antibodies are induced or elicited by the introduction of one or more Chlamydial cell antigens into the vascular system of the animal.

The levels of lipid oxidising antibodies in the vascular system may be elevated relative to levels in a normal uninnoculated animal The one or more *Chlamydia* cell antigens may be isolated antigens or may be comprised on the surface of an isolated *Chlamydia* cell.

The *Chlamydia* cell may be a strain or species which is non-pathogenic in said non-human animal, for example a human *Chlamydia* pathogen as described above.

As described above, a compound identified as a modulator of abzyme activity using an in vitro screen as described above may be testing for activity in a non-human animal model.

A method as described above may include the step of;

introducing a test compound to the vascular system of an animal model as described above and;

determining the activity and/or level of lipid oxidising antibodies in said vascular system.

A decrease in the level of lipid oxidising antibodies following said introduction is indicative that said test compound is a modulator of the activity and/or level of lipid oxidising antibodies.

Alternatively, a primary screen as described above may be performed in an animal model e.g. a lipid oxidising antibody and a test compound may be contacted in the vascular system of an animal model and the lipid oxidation activity of said lipid oxidising antibody may be determined. Alternatively, the level or amount of lipid oxidising antibody may be determined in said vascular system or another biological parameter such as size and number of atherosclerotic lesions may be determined.

A method of identifying a test compound as an agent which modulates the level and/or activity of a lipid oxidising antibody, comprising:

(a) introducing a test compound into the vascular system of an animal having elevated levels of lipid oxidising antibodies; and (b) determining the level or activity of said lipid oxidising antibodies whereby said test compound is a modulator of the level and/or activity of the lipid oxidising antibody when a lack of lipid oxidising antibodies or a decrease in the activity or level of said antibodies in the presence of said test compound is detected.

A method of producing a modulator of lipid oxidising antibody binding and/or activity may comprise the further step of;

selecting said test compound which is a modulator of lipid oxidising antibody binding and/or activity.

Such a method may further comprise the step of;

formulating said selected test compound which is a modulator with a pharmaceutically acceptable excipient.

In addition, methods as described above may comprise the further step of sacrificing the non-human animal.

The present invention encompasses a compound identified using an assay method described above as an agent which modulates (e.g. inhibits) the activity of a lipid oxidising antibody, a pharmaceutical or veterinary composition, medicament, drug or other composition comprising such a compound, a method comprising administration of such a composition to a patient, e.g. for treatment (which may include preventative treatment) of atherosclerotic conditions, use of such a compound in manufacture of a composition for administration, e.g. for treatment of an atherosclerotic condition, and a method of making a pharmaceutical or veterinary composition comprising admixing such a compound with a pharmaceutically acceptable excipient, vehicle or carrier, and optionally other ingredients.

An inhibitor of a lipid oxidising antibody obtained by an assay method as described herein may inhibit the binding of a lipid oxidising antibody to a lipid antigen (i.e. block the binding site of the abzyme) or may inhibit the lipid oxidising activity of the antibody (i.e. block the catalytically active centers).

Inhibitors which block the catalytically active centres of the abzymes may include metal chelators, examples of which are shown in Table 7. Metal ions of transient valence at the catalytic centre of an abzyme are specifically targeted by such chelators to neutralise the catalytic properties of the abzyme. Metal chelators which inhibit abzymes include aspirin.

Other such inhibitors include substrate antagonists which prevent binding of the abzyme with its target epitope(s) in the organism of the host. Binding antagonists may be either be peptide, lipid, polysaccharide, or any other synthetic or naturally occurring product which imitates an epitope of the abzyme. Such an antagonist may be modeled on a lipid antigen, which may for example be a host, i.e. a human antigen or a Chlamydial cell antigen.

The active centre of an abzyme may be modified in other ways to inactivate its catalytic properties. For example, the active centre of an abzyme may contain a photo-(UV-)sensitive group(s) which may be modified by an extra-corporal (UV)irradiation of plasma/serum to inactivate the lipid peroxidation properties of these molecules.

Examples of inhibitors which block the binding sites of the abzymes include anti-idiotypic antibody molecules, including Fab/Fv or other antibody fragments and derivatives, or peptide molecules presenting the fragment(s) of the complementary loop of their active centres (i.e. which imitate the anti-idiotypic antibody molecule) which would enable them to inhibit the binding of the abzymes with their target antigens. Suitable antibody molecules may be made by using a polyclonal or monoclonal strategy or by phage display.

Other compounds with antagonistic properties may be used to compete with antigen for the binding site of an abzyme for example, a peptide, lipid, polysaccharide, or any other synthetic or naturally occurring product which mimics an epitope to which the abzyme binds. Other compounds or chemical and physical procedures with can modify binding sites of the abzymes may also be used to disrupt binding, for example, irradiation as described above.

A method of making a pharmaceutical composition may comprise, identifying a compound as inhibitor of a lipid oxidising antibody using a method described herein, synthesising, preparing or isolating said inhibitor and admixing the inhibitor with a pharmaceutically acceptable excipient, vehicle or carrier, and optionally other ingredients to formulate or produce said composition; and, optionally, determining the lipid oxidation of an antibody as described herein in the presence of said composition.

Such a method may comprise the step of modifying the inhibitor to optimise its properties.

The modification of a known pharmacologically active compound to improve its pharmaceutical properties is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. The design, synthesis and testing of modified active compounds, including mimetics, may be used to avoid randomly screening large number of molecules for a target property.

There are several steps commonly taken in modifying a compound which has a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the lipid oxidising antibody and its lipid antigen are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the modified compound is easy to synthesise, is likely to be pharmacologically acceptable, and does not degrade in vivo, while retaining the biological activity of the lead compound. Modified compounds found by this approach can then be screened to see whether they have the target property, or to what extent they exhibit it. Further optimisation or modification can then be carried out to arrive at one or more final compounds for in vivo or clinical testing.

Whether it is a polypeptide, peptide, nucleic acid molecule, small molecule or other pharmaceutically useful compound that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Aspects of the present invention will now be illustrated with reference to the accompanying figures described above and Tables and experimental exemplification below, by way of example and not limitation. Further aspects and embodiments will be apparent to those of ordinary skill in the art.

All documents mentioned in this specification are hereby incorporated herein by reference.

Table 1 contains data showing the effect of the IgG fraction extracted from human atherosclerotic lesion on lipid peroxidation of *Chlamydia* bacteria; pH 5.7; all measurements made in triplicate.

Table 2 contains data showing the cross-reactivity for lesion IgG between human serum lipoproteins and ovine strain of *Chlamydia psittaci;*

Table 3 contains data showing the effect of feline *Chlamydia* on lipid peroxidation in human serum; all measurements made in triplicate.

Table 4 contains data showing the role of IgG in the initiation of lipid peroxidation by ovine *Chlamydia* in human plasma; all measurements made in triplicate.

Table 5 contains data showing the effect of the addition of ovine *Chlamydia* into the control sera and in the sera of patients with clinical complications of atherosclerosis.

Table 6 shows the inhibition of lipid oxidizing activity of atherosclerotic lesion IgG by antioxidant inhibitors.

Table 7 shows examples of metal chelators which may be used in accordance with the present invention.

Table 8 shows examples of anti-microbials which may be used in accordance with the present invention.

Table 9 shows examples of anti-oxidants which may be used in accordance with the present invention.

Table 10 shows levels of lipid oxidising anti-*Chlamydia* antibodies in healthy and infected sheep (figures in brackets represent % increase/decrease against control).

Table 11 shows the inhibition of abymes using metal chelators.

Table 12 shows the inhibition of in vitro abzyme activity using metal chelators.

Table 13 shows the effect of aspirin on the activity of anti-*Chlamydia* abzymes in patients with Coronary Heart Disease.

Table 14 shows the effect of aspirin on the activity of anti-*Chlamydia* abzymes in patients with Silent Myocardial Ischaemia.

Table 15 shows abzyme activity in patients treated with anti-microbial agent.

Table 16 shows abzyme activity in patients treated with an anti-microbial agent plus aspirin daily.

Table 17 shows the clinical condition of patients treated with anti-microbial agent only.

Table 18 shows average abzyme levels in groups of individuals suffering from atherosclerosis related conditions.

Table 19 shows individual abzyme levels in patients suffering from angina, who were either receiving or not receiving aspirin.

Table 20 shows the induction of abzymes in rabbits inoculated with *Chlamydia*.

Table 21 shows the effect of formalin treated *Chlamydia* in rabbits having induced abzymes.

Table 22 shows anti-*Chlamydia* abzyme activity in patients treated by azithromycin, 500 mg daily (therapy group A).

Table 23 shows anti-*Chlamydia* abzyme activity in patients treated by azithromycin, 500 mg, plus aspirin, 250 mg, daily (therapy group B).

Table 24 shows anti-*Chlamydia* abzyme activity in patients treated by azithromycin, 500 mg daily plus antioxidants (therapy group C).

Table 25 shows anti-*Chlamydia* abzyme activity in therapy group D patients treated by aspirin, 250 mg daily (therapy group D).

Table 26 shows anti-*Chlamydia* abzyme activity in the patient control group.

Table 27 shows a summary of the results of anti-abzyme therapy.

Table 28 shows an evaluation of the severity of angina pectoris by modified Rose-Blackburn Questionnaire before and after treatment.

Table 29 shows abzyme and Rose-Blackburn Test scores before and after treatment for IHD patients who tested negative for anti-*Chlamydia* IgG.

Table 30 shows the inhibitory properties of azithromycin on abzymes

Table 31 shows the effect of various drugs on anti-*Chlamydia* abzyme activity.

Table 32 shows the effect of anti-abzyme therapy on thrombosis and blood clotting

EXPERIMENTS

Materials and Methods

Samples 3 samples of sera were used from 22 patients with clinical complications of atherosclerosis admitted for coronary artery and abdominal aorta by-pass operations in the Cardio-Vascular Surgery Centre of the Clinical Hospital No.1 in Rostov-na-Donu, Russia.

20 of these patients were male and 2 female, aged between 47 and 66. One of these patients, No.6/6a had an acute myocardial infarction at the moment of the testing, hence in some final calculations the data from this patient were not included. The control group was comprised of clinically healthy volunteers 5 of whom were male and 5 female aged between 40 and 55.

Pieces of atheromas from abdominal aorta from 7 of these patients were used to extract IgG fraction by a protein A sorbent as described below.

Extraction of IgG from Atherosclerotic Lesion

The pieces of aorta (approximately 200-400 mg wet weight) were cut into pieces of approximately 10 mg each, placed in 5.0 ml of PBS with 1% non-ionic detergent IGEPAL (octylphenoxypoly(ethyleneoxy)ethanol) CA-630 and homogenised by a mechanical homogeniser (ULTRA-TURRAX) at full-power with a 15 mm probe three times for 3 seconds each with 20 second cooling intervals. After homogenisation the insoluble components were separated by centrifugation at 5000 g for 10 minutes and supernatants were used for analysis.

The supernatant was treated with protein A attached to cross-linked 4% beaded agarose at 37° C. for 30 minutes. The immunoglobulin fraction attached to the beads was then spun down at 5000 g for 10 minutes and the supernatant decanted. In order to remove any lipoproteins attached to the sedimented immunoglobulins, the samples were re-suspended with 10% of IGEPAL (octylphenoxypoly(ethyleneoxy)ethanol) CA-630. They were then centrifuged at 5000 g for 10 minutes and the supernatant was decanted.

To remove the detergent three subsequent washings were performed in the excess of the phosphate buffer with centrifugation under the same regime. The removal of lipoprotein from the immunoglobulin fraction was confirmed by the absence of cholesterol in this fraction.

Determination of Anti-*Chlamydia* Abs

Blood was collected from an ante-cubital vein in the morning after an overnight fast, serum was separated and frozen at −20° C. prior to being tested.

The presence of anti-*Chlamydia* antibodies was measured in the agglutination reaction with ovine *Chlamydia* cells and by ELISA (recombinant antigen-based) assays.

For the agglutination reaction, gradual dilutions of the tested sera were incubated for 24 hours at 37° C. with $10^6$ of live ovine *Chlamydia*. The appearance of aggregates was detected and estimated at 700 nm. The ELISA assay was performed in accordance with manufacturer's instructions (Medac).

A titre $\geq$1:64 was considered to be seropositive.

Determination of Peroxidation of Lipids

Lipid peroxidation was assessed as a level of MDA concentration which was measured by spectrophotometric method [Draper, H. H. et al Free Radic. Biol. Med. (1993) 15, 353]. This method is based on the formation of a coloured product when malondialdehyde reacts with thiobarbituric acid.

Cross Reactivity between Serum Lipoproteins and *Chlamydia*

The IgG fraction comprising anti-*Chlamydia* abzymes was extracted from a human atherosclerotic lesion as described above. 100:1 of this fraction (containing 1:g/ml) was pre-incubated with 890:1 of whole or delipidated serum from a healthy donor for 1 hour at 37° C.; pH 5.7.

Lipoproteins (and associated material) were removed from the serum by preparative ultra-centrifugation in KBr solution in accordance with the earlier described method [Havel R. J et al. J. Clin. Invest. (1955) 34, 1345-1353.22].

$10^5$ *Chlamydia psittaci* cells (Intervet) in a 10:1 volume were then added to the serum. The amount of oxidation induce by contact with the *Chlamydia* cells was then determined using the method described above.

In the presence of binding between the anti-*Chlamydia* abzymes and the plasma lipoproteins, no additional oxidation on contact with the *Chlamydia* cells is observed, because the anti-*Chlamydia* abzymes are removed by the ultracentrifugation.

In the absence of binding between the anti-*Chlamydia* abzymes and the plasma lipoproteins, oxidation is observed on contact of the plasma with the *Chlamydia* cells, because the anti-*Chlamydia* abzymes are still be present in the sample.

Assay for Anti-*Chlamydia* Abzymes

Reagents used in assaying anti-*Chlamydia* abzymes are as follows;

1. Live ovine *Chlamydia* (lyophilised form)
2. PBS (to dissolve bacteria)
3. 0.05M acetate buffer pH 4.0
4. 40% trichloroacetic acid
5. 1 mM 2-thiobarbituric acid.

The presence or amount of catalytic anti-*Chlamydia* antibodies in a sample was detected as follows;

1. Samples of tested sera are diluted 1:1 by 0.05M acetate buffer pH 4.0 to make the final pH of these samples between 5.6-5.8.
2. 990 μl of the diluted serum mixed with 10 μl of the commercial live ovine *Chlamydia* vaccine.
3. Samples are then incubated overnight (12-16 hours) at 37° C.
4. To each sample 250 μl of 40% trichloroacetic acid and 250 μl of 1 mM 2-thiobarbituric acid are added.
5. All samples are placed in a water bath and boiled for 30 minutes.
6. Samples are cooled down and centrifuged at 3,000 g for 10 minutes.
7. Supernatants are collected and their absorption is measured at λ 525 nm to determine the concentration of malondialdehydes (MDA) which are products of lipid peroxidation.

Results

EXAMPLE 1

IgG was extracted from an atherosclerotic lesion in a patient using the method described above. Anti-*Chlamydia* antibodies were found to be present in this IgG fraction (FIG. 1).

The ability of the extracted IgG fraction to oxidize lipid was determined. The IgG fraction was shown to cause a peroxidation of lipids in both ovine and feline strains of *Chlamydia psittaci* (table 1). Kinetic analysis of this peroxidation reaction showed that the reaction had an enzymatic character (FIG. 2, 3). *Chlamydia* bacterium can therefore be considered as a substrate for their antibodies extracted from human atherosclerotic lesion.

The epitopes for anti-*Chiamyidia* abzymes were investigated further using non-ionic detergents. Treatment of *Chiamydia* with TRITON X-100 (non-ionic surfactant, octyl phenol ethoxylate, polyoxyethylene Octyl phenyl ether) or IGEPAL CA-630 (non-ionic surfactant) abolished the oxidation of the lipids in the bacteria by the extracted abzymes. Similar results were obtained for the treatment of human serum low density lipoproteins.

This provides indication that either the epitopes for the catalytic antibodies are conformational and/or the integrity of the antigen is important to initiate the oxidation of lipids in both lipoproteins and *Chlamydia*.

The ability of anti-*Chlamydia* abzymes to cross-react with plasma lipoproteins was then determined. IgG extracted from atherosclerotic lesion was pre-incubated with serum from a patient to allow anti-lipoprotein antibodies in the extract to interact with non-modified lipoproteins. The lipoproteins and antibodies bound thereto were then removed by ultra-centrifugation.

Catalytic anti-*Chlamydia* antibodies were found to be removed with the lipoprotein (Table 2). This demonstrates that the catalytic anti-*Chlamydia* antibodies cross-react with both serum lipoproteins and the ovine strain of *Chlamydia* bacteria.

The presence of anti-*Chlamydia* antibodies in the serum of atherosclerosis patients was then investigated. The addition of ovine *Chlamydia* to the serum of the patients was observed to cause an increase in lipid peroxidation within the sample. A similar effect was observed with a feline *Chlamydia* strain (table 3).

The observed effects were due to presence of lipid oxidising anti-*Chlamydia* antibodies in the fraction of IgG in patient sera (table 4). Catalytic antibodies from the serum of atherosclerosis patients were therefore observed to cross-react with both lipoproteins and ovine *Chlamydia*.

Correlative analysis of the concentration of anti-*Chlamydia* and anti-lipoprotein antibodies in human sera showed that both these parameters have a statistically significant positive link with the high correlation coefficient 0.82. This provides further indication that the same antibody possesses both binding activities.

Figure 4:
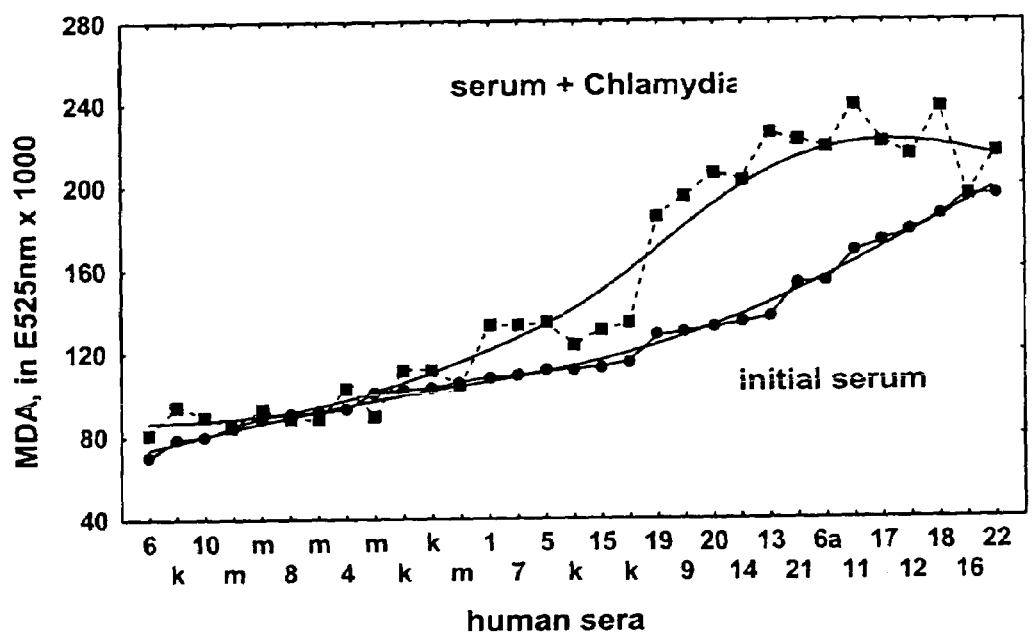
FIG. 4 shows the effect of the addition of ovine *Chlamydia* suspension on lipid peroxidation in human serum. 10:1 of the bacterial suspension was added to 990:1 of the diluted 1:1 serum; pH 5.7; all the mixed samples were incubated at 37° C. for 18 hours (numbers of sera are the same as in table 5).

In studies, with atherosclerosis patients using the assay method described above, catalytic anti-*Chlamydia* antibodies were found in 81% of the patients with clinical complications of atherosclerosis and only in 10% of the control group (FIG. 4, table 5). This demonstrates that these antibodies are a pathogenic marker of this disease.

This study demonstrates for the first time the existence of anti-lipids/lipoproteins abzymes in biological systems. Their occurrence in atherosclerosis but not in healthy individuals indicates that these abzymes play an important role in the pathogenesis of this disease and its complications. It can also interlink such main biochemical/immunological disorders as the activation of lipid peroxidation, the occurrence of anti-lipoprotein antibodies and *Chlamydia* infection, all of which are involved in the development of atherosclerosis.

The presence of lipid-oxidising anti-*Chlamydia* antibodies in the plasma of an individual indicates that the pathological changes specific for this disease have already started. Since these abzymes are responsible for a lipid/lipoprotein oxidation and this process usually correlates with the degree/intensity of generalisation of atherosclerosis, the level/activity of anti-lipid-abzymes reflects the severity of this disease.

Changes in the lipoprotein profile and the elevation of the total cholesterol in plasma/serum are the only specific risk factors established for atherosclerosis. However, these changes can be detected for only 10-15% of all patients with clinical complications of this disease. Detection of lipid-oxidising anti-*Chlamydia* antibodies is the second specific marker for atherosclerosis, but has a much higher diagnostic value than the measurement of the lipid parameters described above.

The methods herein are therefore widely applicable in the diagnosis and prophylaxis of atherosclerosis and related conditions.

EXAMPLE 2

Inhibition of Lipid Peroxidation Human Specimens

Antibodies were extracted from advanced atherosclerotic lesions of human aorta retrieved from four male patients, age range 53-64, during bypass surgery of an abdominal aortal stenosis at the Centre of Cardio-Vascular Surgery of Clinical Hospital No.1 in Rostov-na-Donu, Russia. After recovery these samples were immediately put in 30% w/v solution of NaCl and stored at 0-4° C. for 1-2 weeks prior to examination.

In control experiments, it was shown that during this period the activities of such enzymes as trypsin, catalase, superoxide dismutase, glutathione peroxidase, creatine kinase and lactate dehydrogenase, together with a level of immunoglobulin (IgG) fragmentation and the degree of lipid peroxidation (concentration of malonaldehydes) did not significantly change.

The pieces of aorta (approximately 200-400 mg wet weight) were cut into pieces of approximately 10 mg each, placed in 5.0 ml of PBS with 1% non-ionic detergent IGEPAL (octylphenoxypoly(ethyleneoxy)ethanol) CA-630 and homogenised by a mechanical homogeniser (ULTRA-TURRAX) at full-power with a 15 mm probe three times for 3 seconds each with 20 second cooling intervals. After homogenisation the insoluble components were separated by centrifugation at 5000 g for 10 minutes and supernatants were used for analysis.

Antibody Extraction

The antibodies were extracted and analysed separately from the lesions of the four pieces of the abdominal aorta obtained from the four different patients.

The first step was the treatment of the supernatant with protein A attached to cross-linked 4% beaded agarose at 37° C. for 30 minutes. After that the immunoglobulin fraction attached to the beads was spun down at 5000 g for 10 minutes. The supernatant was decanted. In order to remove any lipoproteins attached to the sedimented immunoglobulins, the samples were re-suspended with 10% of IGEPAL (octylphenoxypoly(ethyleneoxy)ethanol) CA-630. They were then centrifuged at 5000 g for 10 minutes and the supernatant was decanted. To remove the detergent three subsequent washings were performed in the excess of the phosphate buffer with centrifugation under the same regime. The removal of lipoprotein from the immunoglobulin fraction was confirmed by the absence of cholesterol in this fraction.

Lipoproteins

Low density lipoproteins, d=1.030-1.050, were obtained from the plasma of healthy donors by sequential preparative ultracentrifugation in KBr solution in accordance with the earlier described method [Havel R. J. et al J. Clin. Invest. (1955) 34, 1345-1353]. LDL can be already associated with plasma immunoglobulins in these preparations [Bauer B. J. et al Atherosclerosis (1982), 44, 153-160].

These immunoglobulins can potentially either interfere with a reaction between LDL and their antibodies attached to the protein A, or can be bound by the latter protein itself. To avoid these possible artefacts, it was important, before the titration of lipoproteins with lesion antibodies in the affinity tests, to remove LDL with antibody attached using a saturated amount of protein A agarose beads.

In order to determine the level of LDL (in terms of cholesterol concentration), the calibration curve was made for every new batch of lipoproteins and during every new experiment.

LDL Peroxidation by Lesion IgG

Samples of LDL with or without (control) tested antioxidants were incubated with lesion IgG for 16 hours at 37° C. at pH 5.6. The level of lipid peroxidation, in terms of the concentration of malondialdehyde (MDA), was measured by the following procedure. To 1.0 ml of each sample were added 250 µl of 40% trichloroacetic acid and 250 µl of 1 mM 2-thiobarbituric acid. After boiling the samples in a water bath for 30 minutes, they were cooled down and centrifuged at 3,000 g for 10 minutes. Supernatants were collected and their absorption measured at λ 525 nm.

The results of this experiment are presented in Table 6.

A range of inhibitors with antioxidant activity were observed to reduce the lipid oxidation activity of antibodies isolated from atherosclerotic plaques below the limit for detection in this assay. All these compounds therefore inhibit the activity of lipid oxidizing antibody.

Isolated abzymes were assayed in vitro for catalytic activity as described herein in the presence various anti-oxidant inhibitors of the following classes:

Iron ($Fe^{2+}$) chelators—tetracycline

Copper ($Cu^{2+}$) chelators—DDC, aspirin and penicillamine

General metal chelators—CN—, N3, DTPA (chelates free ions only) and picolinic acid.

Results are shown in Table 11.

These results show that abzyme inhibition occurs through copper chelation rather than iron chelation. Three separate copper chelators were demonstrated to block activity and these results suggest that the abzymes contact a bound copper ion as catalytic centre.

EXAMPLE 3

Clinical Example of Reduction in Lipid Oxidising Anti-*Chlamydia* Antibody Activity Patient—A. M. P., Caucasian, male, 43 years old, having clinical symptoms resembling the early stages of angina pectoris with complaints of transient unprovoked chest pain in combination with breathlessness. However, an ECG revealed no pathological changes in the heart.

The results of a blood test on 27 of Dec. of 2000 revealed normal total cholesterol and LDL-cholesterol levels; titers of anti-*Chlamydia* IgG and IgA antibodies were both 1:64 (ELISA, Medac). However, lipid-oxidising anti-*Chlamydia* abzymes were detected and their activity was 32 µM MDA (mean figure of triplicate measurement) per 1 ml of his serum.

The following daily treatment, over the course of three months, was recommended: Tetracycline hydrochloride 500 mg in combination with an antioxidant cocktail—Vitamin E 20 mg, Vitamin A 1.5 mg, Vitamin B6 3.2 mg, Ascorbic acid 180 mg, Zinc Gluconate 30 mg, L-Selenomethionine 100 µg per.

In three months after the beginning of the therapy complaints of chest pain and breathlessness disappeared. At the end of March, at the end of the treatment and almost exactly 3 months after treatment started, the analysis of his serum showed no changes in anti-*Chlamydia* IgG and IgA antibody titers (1:64 (ELISA, Medac)). At the same time the presence of anti-*Chlamydia* abzymes was not detectable.

Two weeks later the test was repeated with the same result.

EXAMPLE 4

The Influence of Ovine *Chlamydia* on Lipid Peroxidation of Ovine Sera

Sheep were vaccinated with Chlamydial cells using standard techniques and tested for abzyme activity. The results are set out in Table 10.

Pre-vaccinated sheep were disease-free and healthy and showed no significant changes between assay levels with and without *Chlamydia*.

Post-vaccination, sheep showed very high levels of anti-*chlamydia* antibodies but insignificant/no levels of abzymes.

Post abortion (wild type) represents sheep with Chlamydiosis disease which have aborted due to the occlusion of the vascular system in the uterus: in these, the level of abzyme activity verified by the addition of *Chlamydia* is significantly higher than without *Chlamydia*.

These results show that adminstration of Chlamydial vaccine may reduce or prevent the production of lipid oxidising antibodies.

EXAMPLE 5

The Association of Abzyme Activity and Arterial Stenosis

The activity of lipid-oxidising anti-*Chlamydia* antibodies and the degree of arterial stenosis in two different clinical groups was investigated. The first was a group of patients with Ischaemic Heart Disease (IHD) and the second a group of patients with Ischaemic Cerebrovascular Disease (ICD).

Coronary Artery Stenosis

Figure 5:
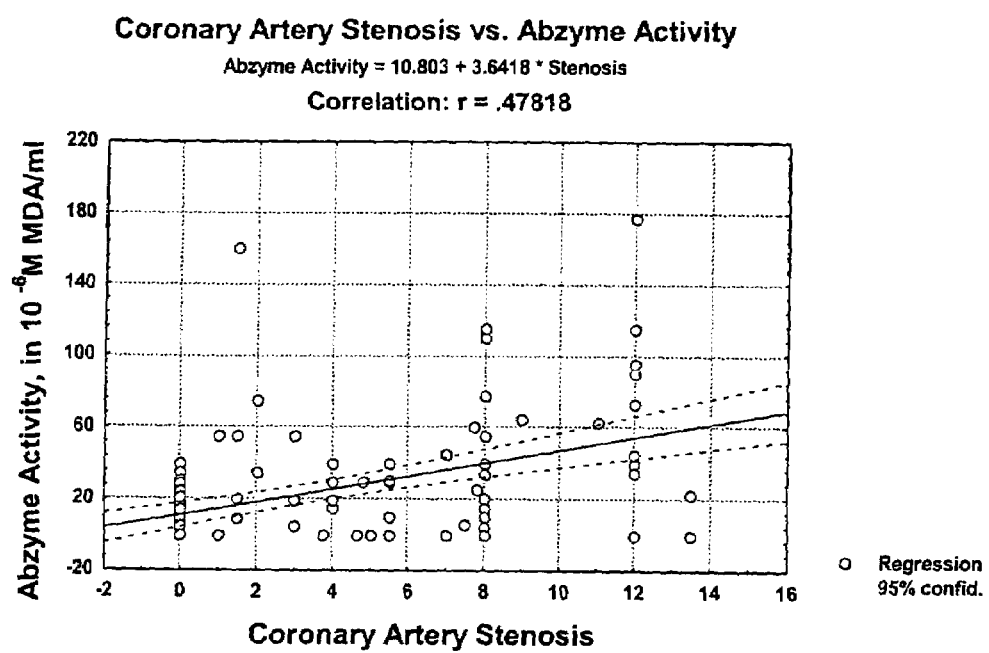
FIG. 5 shows the correlation between the degree of coronary artery stenosis and the activity of lipid-oxidising anti-*Chlamydia* antibodies in IHD patients. Severity of the stenosis is presented in terms of a score, which was calculated as an integral parameter of the stenosis of coronary arteries estimated by angiography.

The preliminary results of the trial show a positive and significant correlation between the activity of the anti-*Chlamydia* abzymes and the severity of the stenosis of coronary arteries of patients with IHD (FIG. 5).

Figure 6:
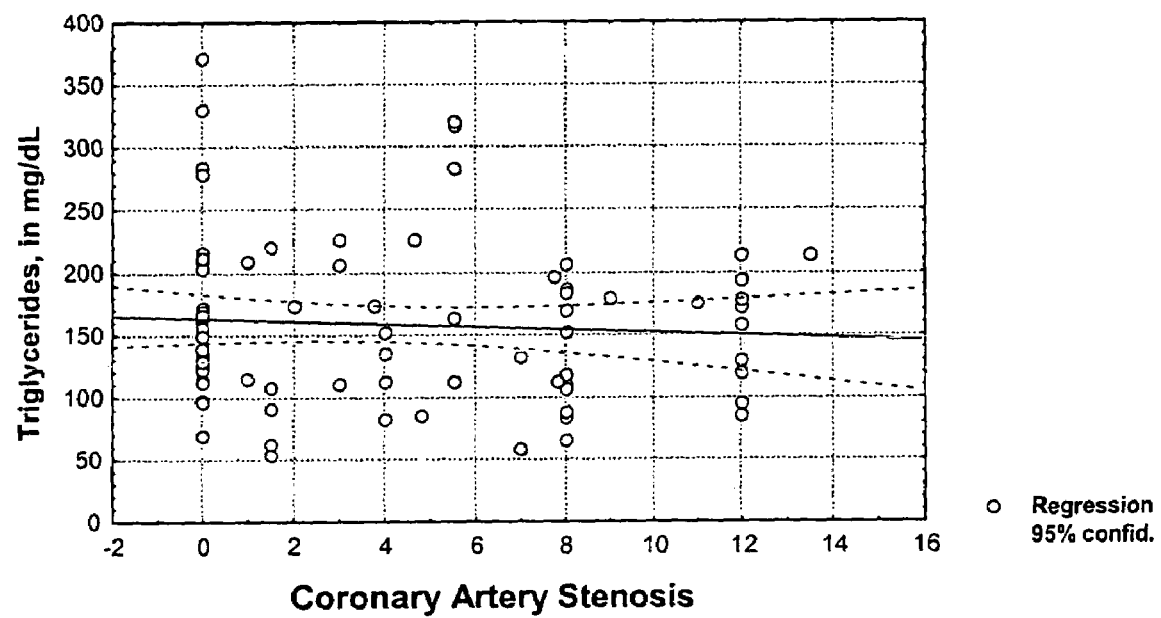
FIG. 6 shows the relationship between the degree of coronary artery stenosis and triglycerides concentration in IHD patient sera.
Figure 7:
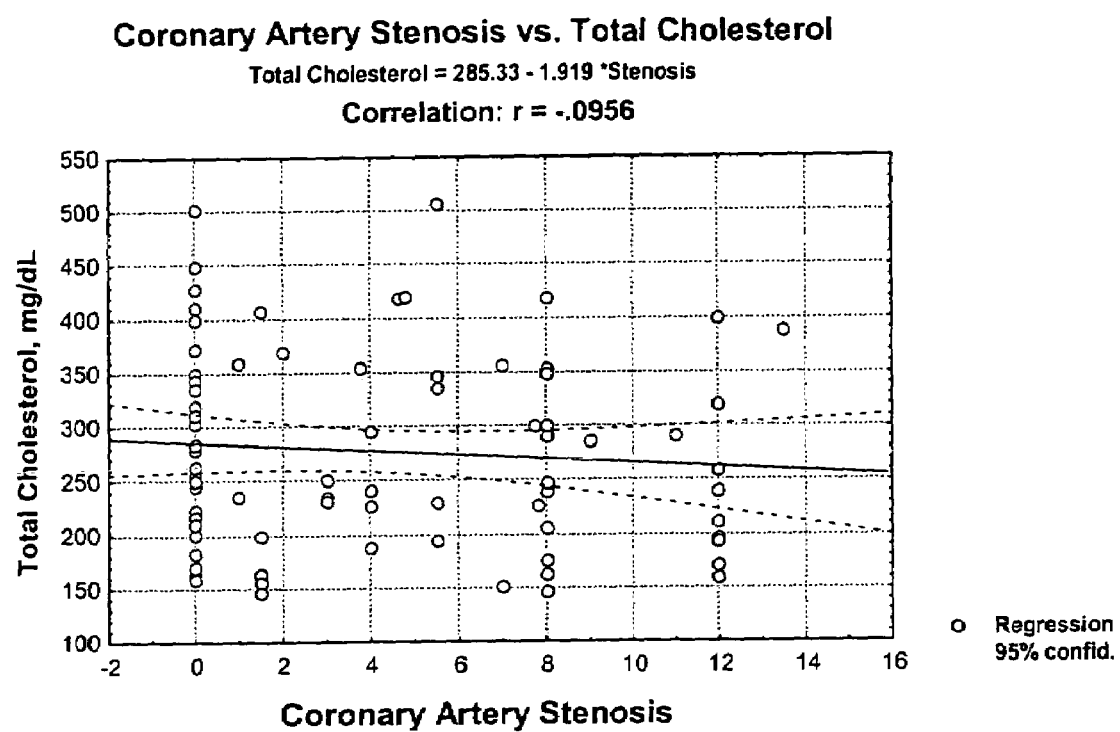
FIG. 7 shows the relationship between the degree of coronary artery stenosis and total cholesterol concentration in IHD patient sera.
Figure 8:
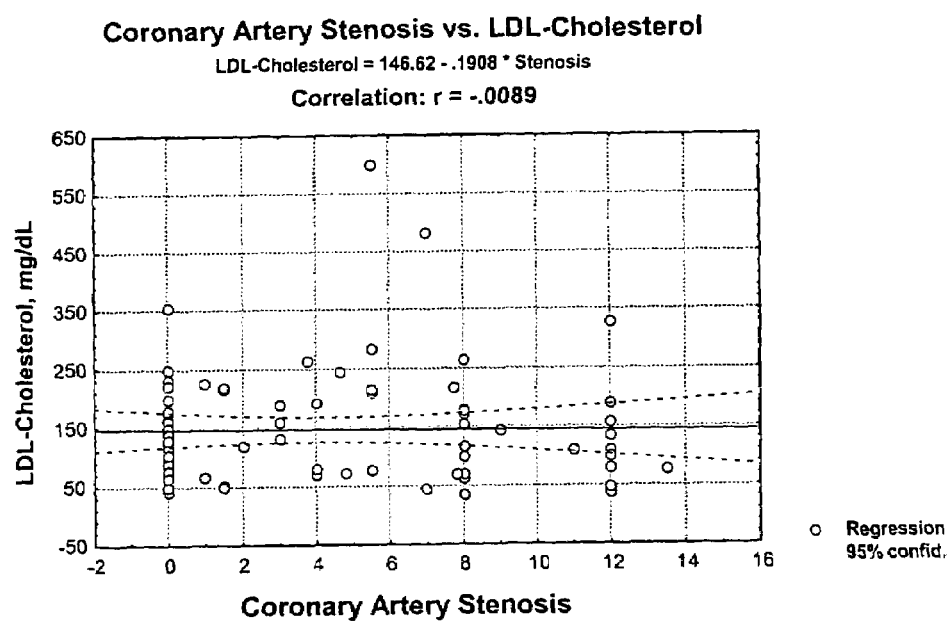
FIG. 8 shows the relationship between the degree of coronary artery stenosis and LDL-cholesterol concentration in IHD patient sera.

No links was observed between the degree of coronary stenosis and such serum lipids as triglycerides, total cholesterol and cholesterol of low density lipoproteins, LDL-cholesterol (FIGS. 6, 7, 8)

Cerebral Artery Stenosis

Figure 9:
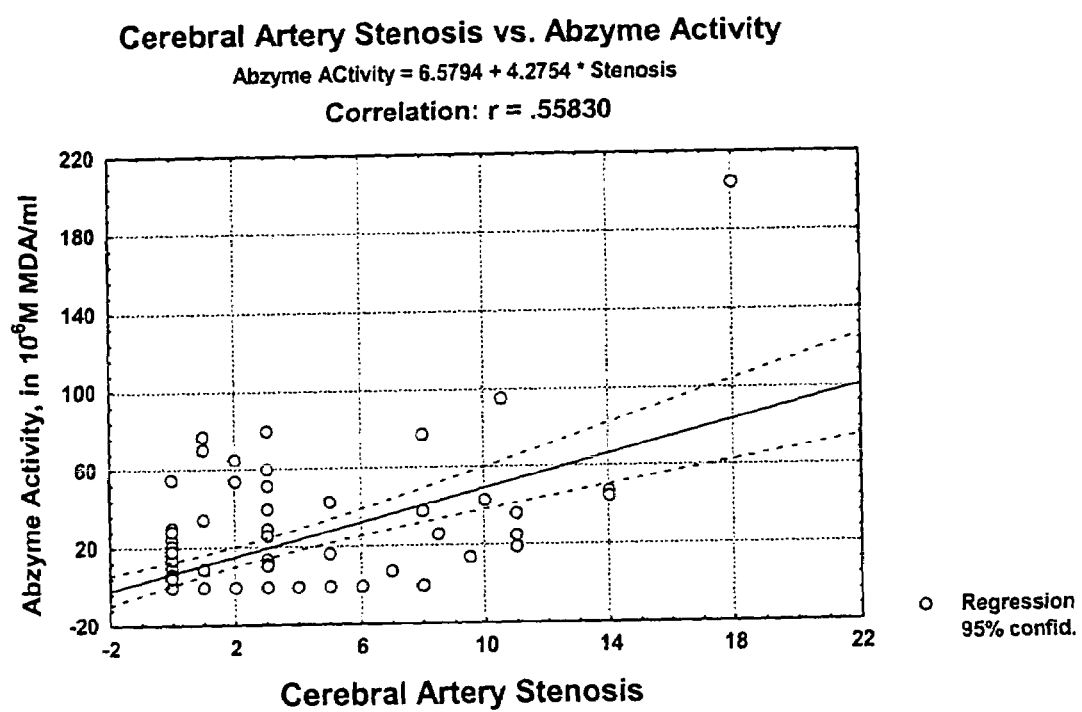
FIG. 9 shows the correlation between the degree of cerebral artery stenosis and the activity of lipid-oxidising anti-*Chlamydia* antibodies in ICD patient sera. Severity of the stenosis is presented in terms of a score, which was calculated as an integral parameter of the stenosis of cerebral arteries estimated by angiography.

A positive significant correlation between level of the abzymes and arterial stenosis was observed in the group of patients with ICD (FIG. 9).

Figure 10:
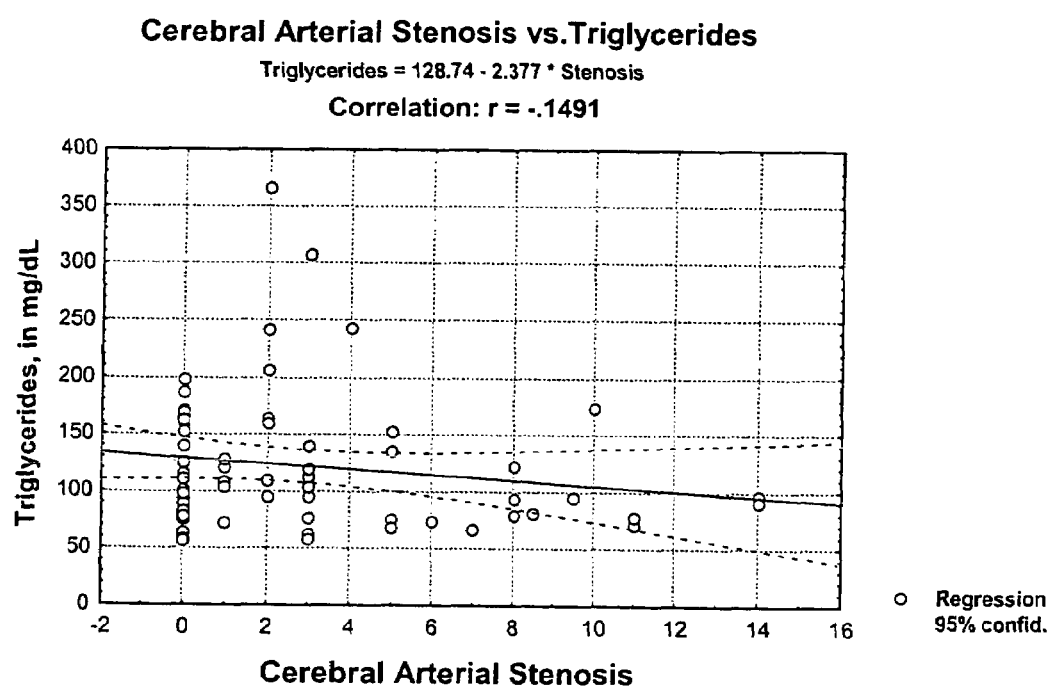
FIG. 10 shows the relationship between the degree of coronary artery stenosis and triglycerides concentration in ICD patient sera.
Figure 11:
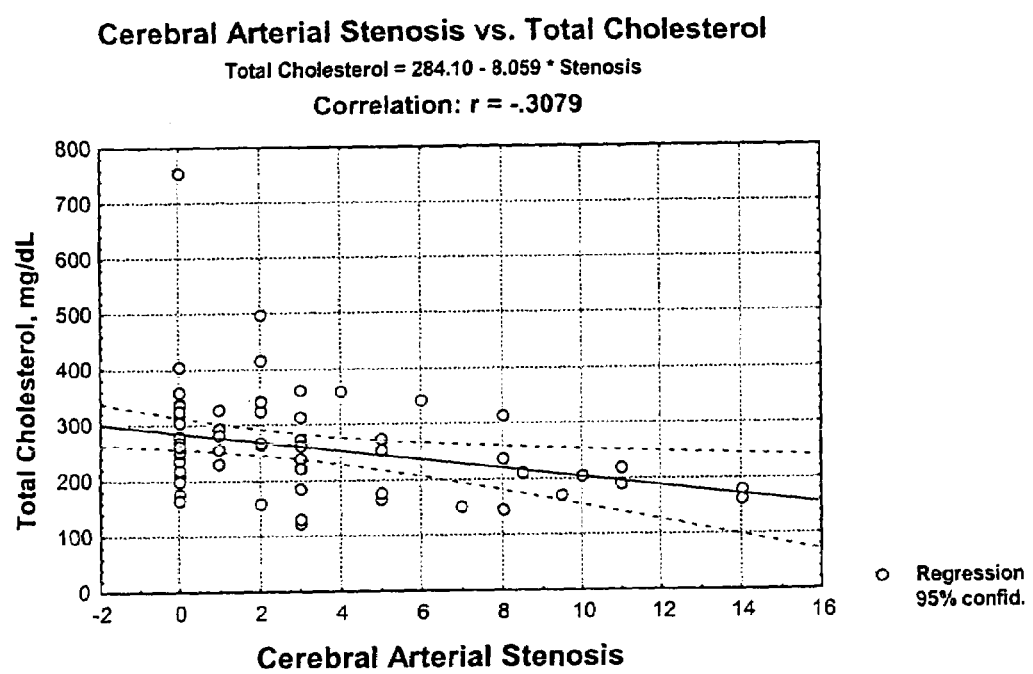
FIG. 11 shows the relationship between the degree of coronary artery stenosis and total cholesterol concentration in ICD patient sera.
Figure 12:
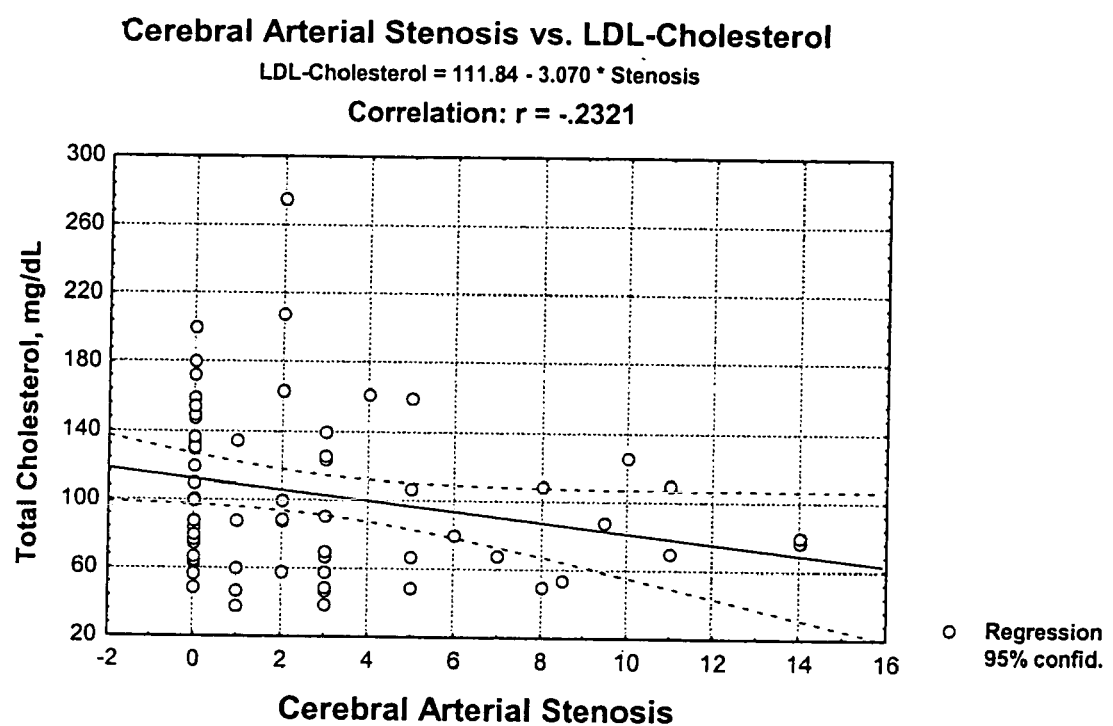
FIG. 12 shows the relationship between the degree of coronary artery stenosis and LDL-cholesterol concentration in ICD patient sera.

As in the IHD patients, of arterial stenosis and serum triglycerides, total cholesterol and LDL-cholesterol (FIG. 10, 11, 12).

These experiments establish a positive link between anti-*Chlamydia* abzyme activity and the degree of stenosis both in heart and brain arteries, and shows that these antibodies are involved both in the initiation and progression of atherosclerosis.

EXAMPLE 6

Inhibition of Abzymes Using Acetylsalicylic Acid (Aspirin)

The data presented in Tables 13 and 14 demonstrate that the activity of anti-Chlamydialipid oxidising abzymes can be inhibited by acetylsalicylic acid (aspirin) when it is administered to humans.

Three patients with Coronary Heart Disease (CHD), whose blood had a significant level of abzyme activity of these abzymes, were treated with 250 mg daily dose of aspirin.

After a week, blood tests of these patents revealed a significant inhibition of the abzyme activity: 5-fold for the one patient and an undetectably low level for the other two (Table 13).

To eliminate the possibility that administration of aspirin in the above experiments coincided with the natural clearance of the abzymes from the bodies of the patients and to investigate the in vivo effect of aspirin on anti-Chlamydial lipid oxidising abzymes, the following experiment was undertaken.

A patient F with Silent Myocardial Ischaemia who was taking regularly 250 mg aspirin daily was identified. The level of the abzymes in the blood of patient F was determined and found to be almost undetectable.

Patient F stopped taking aspirin for a week and the level of abzyme in his blood was determined again. A significant level of lipid oxidising abzymes was found in the serum of patient F.

Patient F resumed the previous regime of 250 mg aspirin daily, and the level of abzymes was determined after 7 day. The level of these abzymes was significantly reduced (Table 14) relative to the level when the patient was not receiving aspirin.

During the course of theses experiments, the patient did not have any respiratory disorder, or signs of any other pathological conditions. This indicates that the recorded variations of the abzyme activity were related to the intake of aspirin by this patient.

In conclusion, the present data show that acetylsalicylic acid inhibits lipid-oxidising anti-*Chlamydia* antibodies in vivo, and, in particular, in patients with clinical complications of atherosclerosis.

EXAMPLE 7

Antibodies Which Cross-React with Chlamydial Cells

A commercially available preparation of antibodies specific for human Apo-B was tested for ability to cross-react with ovine *Chlamydia psittaci* (Intervet).

The anti-apo-B antibody preparation was observed to contain a fraction which also binds to ovine *Chlamydia* (FIG. 13).

Apo-B therefore has an epitope which is identical to an epitope present on the Chlamydial membrane. Antibodies which bind this epitope will cross-react with *Chlamydia* cells and human apo-B.

EXAMPLE 8

The Effect of Anti-Chlamydial Agents on Abzyme Activity in vivo

Patients aged between 45 and 62, with stable angina were treated either with 500 mg azithromycin once per day for 15 days and 30 days or with 500 mg azithromycin, 500 mg, plus aspirin, 250 mg, daily for 15 days.

Abzyme activity before and after treatment is shown for the first group in Table 15 and for the second group in Table 16.

Abzyme activity was shown to be significantly reduced in both groups of patients after 15 days, with the reduction being particularly large in the group treated with azithromycin and aspirin. A reduction in LDL levels was also observed. No adverse reactions were registered in any of the patients.

The clinical condition of patients was also observed to improve over the course of treatment (Table 17).

Administration of the anti-Chlamydial drug azithromycin over two weeks, in particular in combination with aspirin, reduced abzyme activity and improved the clinical condition of patients suffering from angina.

EXAMPLE 9

Abzyme Activity in vivo

Abzyme levels were determined in five sets of people using the methods described herein. A control group were determined to be healthy by present techniques. A silent ischaemia group were individuals who were shown to be ischaemic in an exercise/ECG test but were unaware of any health problems.

Groups of individuals suffering from stable or unstable angina and who had suffered a myocardial infarction were also tested.

The average level of abzymes in each group is shown in Table 18, where n is the number of individuals in each group. Individuals were considered to be positive for abzymes, if a 15% increase in lipid oxidation was observed on addition of *Chlamydia* cells using the methods described herein. The percentage of each group who were positive for abzymes is also shown in Table 18. None of the values in the table has been adjusted for individuals taking aspirin.

The level of abzyme activity and the proportion of individuals testing positive for abzymes is shown to correlate with the severity of the individual's condition. Abzyme activity is observed to drop sharply after a heart attack (compare values for unstable angina and acute phase myocardial infarction). Abzyme activity then rises progressively after the heart attack in surviving patients.

This is indicative of an active role for abzymes in the induction of a myocardial infarction. Abzymes may form part of the agglutination mechanism of the thrombolytic clots which block blood vessels and produce the infarction. This agglutination into clots reduces the detectable abzyme activity in the vascular system. As the clot dissolves post-infarction, detectable abzyme activity increases.

EXAMPLE 10

The Effect of Aspirin on Abzyme Activity in vivo

Abzyme activity was determined in groups of individuals with class I, II and III stable angina or unstable angina using the methods described herein. Individuals were also questioned as to whether they were taking aspirin. Individuals were sub-grouped according to whether they reported taking aspirin and the results are shown in Table 19. These results are not adjusted for individuals taking aspirin but not reporting it.

The figures shown in Table 19 are values of abzyme activity of individuals in each group (i.e. class I aspirin takers and non-aspirin takers etc).

These results show that abzyme levels correspond to the severity of the disease. Aspirin takers generally have lower abzyme activity than non-aspirin takers with the same clinical symptoms.

EXAMPLE 11

Animal Model for Atherosclerotic Disorders

Rabbits were infected with *Chlamydia psittaci* (Lori strain) by the intra-tracheal route with 1.5 mls of 10% suspension of chicken embryo containing $1\times10^{7.5}$ of *Chlamydia* cells. The sera of the rabbits was collected at day 0 (pre-infection) and then every 14 days thereafter, by using the standard blood collection route from the heart.

The sera was then used in a standard ELISA assay to measure the titre of anti-*Chlamydia* IgG. On the same sera samples, the amount of *Chlamydia* abzyme level was measured using the standard assay described previously. The appearance of abzymes correlates with the appearance of anti-*Chlamydia* IgG antibodies.

Results for 4 rabbits (3 infected and 1 control) are shown in Table 20.

These results show that an animal model with high abzyme levels can be generated by infection with *Chlamydia*. These models are useful in following the progression of disease caused by abzymes and determining various parameters such as rate of clearance. Models are also useful in testing compounds as potential drugs for the reduction of abzyme levels and concomitant improvement in symptoms.

EXAMPLE 12

Anti-*Chlamydia* Abzymes In Rabbits

The production of lipid-oxidising anti-*Chlamydia* antibodies was demonstrated using a rabbit model produced as described above by intra-tracheal infection with *Chlamydia Psittaci*.

Results are shown in Table 21. Rabbits were infected intra-tracheally with 1.5 ml of 10% suspension of chicken embryo containing $1\times10^{7.5}$ of *Chlamydia Psittaci* (Lori strain) and blood was collected from the rabbit hearts. Abzyme levels on $7^{th}$ day after a subcutaneous injection of a vaccine, formalin treated $1\times10^{7.5}$ *Chlamydia Psittaci* (Lori strain) are shown (§ table 21).

The appearance of abzymes coincided with the accumulation of anti-*Chlamydia* IgG detected as detected by ELISA. An injection of the same bacteria, but in formalin treated preparation, on the $14^{th}$ day of the infection (rabbit 3) led to an increase in the ELISA anti-*Chlamydia* IgG titers on the $7^{th}$ day after this inoculation. At the same time, in the serum of this rabbit there was a 2-fold reduction in the abzyme activity, from 131 to 64 µM MDA/ml.

There was no such reduction in the abzyme activity registered for two other rabbits, which did not receive this inoculation.

Inoculation of the vaccine preparation of the *Chlamydia* antigen was thus observed to reduce the presence/activity of anti-*Chlamydia* abzymes.

EXAMPLE 13

Anti-Abzyme Therapy in Ischaemic Heart Disease

A group of 30 patients with ischaemic heart disease (IHD) was selected for experimental therapy to reduce/eliminate the activity of anti-*Chlamydia* abzymes in their serum (the therapy group) and a group of 20 'matched' patients were not treated (the untreated Patient Control Group). The trial took place in Saratov Cardiological Centre (Russian Federation) from June until August 2002.

The therapy group comprised 23 male and 7 female patients with an average age of 55±1.1 years. The patients control group for monitoring of the abzyme level comprised 20 patients with IHD, of which 15 were male and 5 were female patients with an average age of 53±1.2 years. Each patient gave written consent for his/her participation in the trial.

All patients had angina of II-III class of Canadian Cardiological Society classification. 15 patients in the therapy group and 10 in the patient control group had a history of myocardial infarction in the past year. IHD diagnosis for the other 15 patients in the first group and 10 in the patient control group was confirmed by coronary angiography, which detected 70% or more of arterial stenosis.

Apart from the degree of the generalization or severity of atherosclerosis, all groups were matched not only on age, gender and risk factors but also on medication, nitrates, β-blockers, angiotensin-converting enzyme inhibitors etc.

The progression of the clinical condition of the patients was monitored by the use of the modified Bruce Protocol for treadmill exercise/stress ECG testing and on the Rose-Blackburn Questionnaire (Cardiovascular Survey Methods. WHO, Geneva, 1968).

The main parameter of the selection of a patient for the trial was a level of anti-*Chlamydia* abzyme activity in excess of 15 µM of malondialdehyde (MDA) per ml of serum. The therapy group was split into 4 therapeutic sub-groups:

1.) Therapy group A—those given a nonspecific inhibitor of anti-*Chlamydia* abzymes, azithromycin, which also has anti-microbial properties, was prescribed in the dose of 500 mg daily.
2.) Therapy group B—a combined administration of azithromycin, in the same dose, with acetylsalicylic acid (aspirin) was prescribed. The latter has the apparent ability to block specifically the abzymes via chelating ions of copper in their active centre. The dose of aspirin was 250 mg per day.
3.) Therapy Group C—a combined administration of two types of nonspecific inhibitors of the abzymes with anti-oxidant properties, anti-microbial azithromycin, in the same dose as in the previous groups, and vitamins E, A, C, was prescribed. The daily dose of vitamin E was 30 mg, vitamin A 1,500 EU and vitamin C 90 mg.
4.) Therapy Group D—The patients in this group were given 250 mgs aspirin daily only.

The blood of the patients of all three groups was tested every two weeks. The therapies were continued subject to the efficiency of the suppression/elimination of the anti-*Chlamydia* abzyme activity and the trial results are shown up to up to 60 days after administration of placebo/therapy.

The titre of anti-*Chlamydia* antibodies was measured in the Therapy group using the method previously described (see Table 26). The severity of clinical symptoms was also measured (see Table 28)

Results of the monitoring of the suppression of the anti-*Chlamydia* abzyme activity are presented in the following tables (Tables 22-27).

At first it was noticed that in two weeks of the therapy in all groups there was a significant reduction in the abzyme activity. The most prominent was in the Therapy Group B where the use of a nonspecific inhibitor, azithromycin, was combined with use of a specific inhibitor, aspirin (Table 23). Indeed, the level of the activity in this group reached the level of clinically healthy individuals (see Summary Table 28). An important observation was that patient TGB7 in this group showed a large increase in abzyme level (which correlated with a worsening of clinical symptoms) on the $45^{th}$ hday (double asterix—Table 23) and then after another 15 days of treatment the patient started to feel better and abzymes had reduced to 0. TGB7 also showed an increase in ApoB levels (asterix—see Table 7) at the same time as an increase in abzymes level at 45 days.

The least effective therapy was in the Therapy Group A (azithromycin only—Table 22) where for 27% of the patients (3 out of 11, marked with an asterix) there were no changes in the abzyme activity after 15 days. However, a continued reduction for the majority of the patients was reversed for two of them in the first group on the 30$^{th}$ day of the trial (TGA2 and TGA6, Table 1, marked with two asterixes). This observation, together with the fact that there were some patients with, although reduced, a remaining significant level of the abzyme activity, led to the extension of treatment for another 30 days, resulting in significant decreases in all patients. In therapy group A clinical symptoms of patients TGA2 and TGA6 improved for 15 days and correlated with a reduction in the abzyme level, however clinical symptoms worsened and abzymes level increased around the 30$^{th}$ day of the trial (double asterix—Table 22).

In Therapy Group C (Azithromycin and antioxidants) there was one patient (TGC1) who showed no decrease in abzyme activity (asterixed—Table 24)

The use of aspirin alone, in the prescribed dose, without azithromycin, led to a reduction in the abzyme activity but to a lesser degree than observed with the combination (Therapy Group D—Table 25).

The applied anti-abzyme therapy has significantly improved the clinical condition of the majority of the patients, which was evaluated with the modified Rose-Blackburn Questionnaire (Table 27) and verified by the use of the treadmill exercise/stress ESG testing. At the same time there was no positive clinical dynamic noticed in the control group, even for a single patient. In Table 27 PCG indicates Patient Control Group, § indicates results obtained by immuno-fluorescent assay, §§ indicates results obtained by immuno-enzymatic assay, §§§ indicates results obtained by immuno-turbidimetric assay. * indicates a statistically significant difference.

No statistically significant changes were observed for the following parameters of coagulation: Kaolin Clotting Time, activated Partial Thromboplastin Time, Prothrombin time. There were no changes registered in the level of the serum Creatinine and the liver enzymes Alanine aminotransferase and Aspartate aminotransferase.

No patients in the experimental therapy groups had had positive changes in their clinical conditions for a number of months/years prior to their selection for the trial. Therefore, this absence of positive dynamic can be used as the 'internal' control for the significant clinical progress of the patients which has been observed.

The original intensive regimen of abzyme inhibitor, which has anti-microbial properties, totally eliminated the presence of anti-*Chlamydia* IgG.

By targeting the anti-*Chlamydia* abzymes, significant improvements in lipid concentrations and thrombosis were achieved (Table 27) Therefore, it is possible to suggest that the developing abnormalities in the lipid metabolism and coagulation system in atherosclerosis are secondary to the appearance of these lipid-oxidising catalytic antibodies.

The observed beneficial effect of azithromycin could not be explained by its anti-bacterial properties because only in 15 patients out of 30 (in 50%) selected for the trial had beforehand tested positive on the presence of Chlamydia infection. The level of anti-*Chlamydia* IgG in the serum of another 8 patients was insignificant, below 1:32 in immuno-fluorescent assay. The other 7 patients tested negative.

The diagnostic test indicates whether a patient carries abzymes and is not necessarily correlated with the patient being positive for *Chlamydia* IgG antibodies. Therefore, the therapy should not be prescribed on the basis of seropositivity for *Chlamydia*. This shows the usefulness in the invention when the diagnostic test is linked to administration of the correct therapy followed by repeated prognostic tests to monitor clearance of abzymes using the treatment.

Certain IHD patients in the theranostic trial were negative for anti-*Chlamydia* IgG antibodies but tested positive for abzymes. The abzyme and Rose-Blackburn Test scores before and after treatment for these patients are shown in shown in table 29. These patients were treated and their abzyme activity reduced with a subsequent improvement in clinical symptoms.

These results show that whether a patient carries abzymes is not necessarily correlated with the patient being positive for *Chlamydia* IgG antibodies. An atherosclerotic condition cannot be diagnosed or therapy prescribed on the basis of seropositivity for *Chlamydia*. However, abzymes are shown to be useful as a diagnostic marker of atherosclerotic conditions and may be linked to administration of the appropriate therapy followed by repeated prognostic tests to monitor clearance of abzymes.

EXAMPLE 14

Anti-Abzyme/Antioxidant Properties of Azithromycin

The inhibitory activity of Azithromycin on abzymes isolated from an atherosclerotic lesion was measured as described above. The results are shown in Table 30. Each number is a mean of duplicate/triplicate measurement, and calculated as a difference between the level of MDA accumulation in the tested serum before and after the addition of 0.5 of immunisation dose of ovine *Chlamydia* vaccine ('Intervet'). The effect of DMSO was deducted from the readings where indicated (**).

Azithromycin was found to be a strong in vitro inhibitor of abzyme activity. This activity may be responsible for the in vivo biological effects observed with azithromycin, such as the rapid decrease in abzyme activity after administration of azithromycin.

EXAMPLE 15

Membrane Integrity of *Chlamydia* and Abzyme Activity

Abzyme activity was measured as described above using formalin, ammonium sulphate or SDS treated samples of *Chlamydia pneumoniae* or *Chlamydia Psittaci*. In these reactions, no lipid oxidising reaction in the test system.

Treatment of the *Chiamydia* bacteria with chaotropic agents, including non-ionic detergents 1% TRITON X-100 (non-ionic surfactant, octyl phenol ethoxylate, polyoxyethylene Octyl phenyl ether) and IGEPAL (octylphenoxypoly(ethyleneoxy)ethanol) CA-630, 10% solution of DMSO, which preserve the presence of the membrane lipids in the system but disrupt the integrity of the bacterial membrane, completely abrogated the development of lipid oxidation reaction.

These experiments indicate that lipids are important for the initiation and the development of the reaction(s) of lipid peroxidation developing in the test system. In particular, a role for lipopolysaccharide, which is disrupted by the above treatmemts is indicated.

EXAMPLE 16

Case Histories

Case No 1.

A 64 year old male patient was diagnosed with Ischaemic Heart Disease 3 years ago when he had the first symptoms of angina pectoris. The diagnosis was confirmed by coronary angiography, which established a stenosis of two arteries: 75% of the right coronary artery and 100% occlusion of the anterior intraventricular artery.

He was selected for the theranostic trial on the grounds that abzymes were detected in his serum. A combination of two abzyme inhibitors, azithromycin, in the dose of 500 mg daily, and aspirin, in the dose of 250 mg daily. His level of anti-*Chlamydia* IgG was high with a titer of 1:256.

Before the treatment his clinical condition, estimated by a score of a modified Rose-Blackburn protocol, was 19. The abzyme activity was 25 µM MDA/ml, the level of total cholesterol 226 mg/dL, triglycerides—90 mg/dL, HDL-cholesterol—56 mg/dL, LDL-cholesterol—73 mg/dL, ApoA—139 mg/dL, ApoB—81 mg/dL, alanine aminotransferase (ALT)—25 U/L, aspartate aminotransferase (AST)—29 U/L, creatinine—0.71 mg/dL.

During the treatment there were no significant adverse reactions noticed. On his first visit after the start of the therapy, 15 days, he reported a certain improvement in the signs of his disease. This improvement continued until the 30$^{th}$ day of the therapy. This was supported by an increase in the tolerance time during treadmill exercise ESG testing by modified Bruce Protocol.

At that time neither the abzyme activity nor the presence of anti-*Chlamydia* IgG was detected in his serum. The level of lipid parameters also improved: total cholesterol reduced to 172 mg/dL, triglycerides to —80 mg/dL, HDL-cholesterol—52 mg/dL, LDL-cholesterol—64 mg/dL, ApoA—110 mg/dL, ApoB—67 mg/dL. The level of ALT, AST and creatinine remained the same —25 U/ml, 27 U/ml and 0.7 mg/dL respectively.

On the arrival of the 45$^{th}$ day from the beginning of the therapy he reported that a week before, on the 38$^{th}$ day from the beginning, his condition had started to deteriorate—the frequency and intensity of the angina attacks had suddenly increased. This coincided with a rise in abzyme activity, which reached 80 µM MDA/ml. However, it is important to note, no 'traditional' anti-*Chlamydia* IgG were registered.

At the same time, the parameters of the lipid metabolism also deteriorated: total cholesterol increased to 185 mg/dL, triglycerides—143 mg/dL, LDL-cholesterol—74 mg/dL, ApoA—115 mg/dL, ApoB—87 mg/dL. Level HDL-cholesterol and ApoA remained essentially the same—50 mg/dL and 115 mg/dL, correspondingly. An important observation was that the level of liver enzymes also changed, ALT increased to 35 U/L and AST to 39 U/L; creatinine concentration was 0.8 mg/dL.

However, continued therapy seemed to completely suppress/eliminate the abzyme activity, which was also accompanied by an improvement in the concentration of some lipid parameters: total cholesterol was reduced to 165 mg/dL, triglycerides to —100 mg/dL, mg/dL. Concentration of HDL-cholesterol was 47 mg/dL, LDL-cholesterol—72 mg/dL, ApoA—112 mg/dL. The level of ALT, AST and creatinine became 24 U/ml, 25 U/ml and 0.7 mg/dL respectively.

At the same time the ApoB level remained on the pretreatment level 80 mg/dL. The initially improved clinical condition also returned to the level that it was before the beginning of the therapy, the Rose-Blackburn score was 19. To stabilise the suppressed level of the abzymes with an attempt to improve the clinical parameters of the patient, it was recommended to continue the prescribed anti-abzyme therapy.

No anti-*Chlamydia* IgG was detected in this patient from the 15$^{th}$ day of the start of the therapy onwards and the continued use of azithromycin was aimed at controlling the suppressed level of the cross-reacting abzymes, which bind and oxidise lipoproteins, rather than bacterial infection per se.

Case No.2

A 46 year old male patient was diagnosed with IHD when he was admitted with an acute myocardial infarction on 21 Feb. 2002. Before that he had no history of heart disease. The following May a coronary angiography revealed no stenosis/narrowing of his coronary arteries.

This patient was selected for a theranostic trial on the grounds that significant activity of the anti-*Chlamydia* abzymes was detected in his serum. It was 140 µM MDA/ml. A combination of two types of abzyme inhibitors, azithromycin, in the dose of 500 mg daily, and an antioxidant cocktail of vitamins E, A, C, was prescribed. The daily dose of vitamin E was 30 mg, vitamin A 1,500 EU and vitamin C 90 mg.

There was no detectable level of 'traditional' anti-*Chlamydia* IgA, IgG or IgM detected in the serum of this patient before or during the treatment period.

Before the treatment his clinical condition, estimated by the score of a modified Rose-Blackburn protocol, was 17. The level of total cholesterol was 205 mg/dL, triglycerides—129 mg/dL, HDL-cholesterol—39 mg/dL, LDL-cholesterol—80 mg/dL, ApoA—152 mg/dL, ApoB—221 mg/dL.

During treatment no significant adverse reactions were noticed. He started to feel a certain improvement in signs of the disease after the first two weeks of the treatment. This progress continued through the whole period of the therapy of 60 days. This was supported by a significant increase in the tolerance time during treadmill exercise ESG testing carried out in accordance with modified Bruce Protocol.

At the end of the observation period, after 60 days, neither the abzyme activity nor the presence of anti-*Chlamydia* IgG was detected in his serum.

These changes in abzyme activity coincided with a significant improvement in the clinical condition of the patient. His score on the modified Rose-Blackburn protocol reduced from 17 before the treatment to 13 after it.

EXAMPLE 17

Effect of Anti-Abzyme Therapy on Thrombosis

One of the indicators of atherosclerotic disorders is that patients often present with aberrations in the time it takes for their blood to form clots (this is generally increased in patients). A number of pathways can lead to clot formation and therefore there are four internationally recognized tests for clotting time. The first is called Activated Partial Thromboplastin Time (APTT) and works by adding thromboplastin and calcium to measure the intrinsic pathway. The second called Prothombin Time (PT) is a simple measurement for the extrinsic pathway. Silica clotting time (SCT) measures clotting induced by fine particles (silica) and Kaolin Clotting Time (KCT) measures clotting induced by larger particles (Kaolin). For all these fast clotting times are indicative of higher risk of thrombosis.

Before treatment, the clotting times using all four methods for all patients in all therapy groups were measured and the mean calculated with a standard error. Measurements were repeated 60 days later. Controls were our Patient Control Group (measurements taken once—values did not change significantly for these patients over time) and also form our clinically healthy control group. The results of treatment are shown in Table 32.

The average value for patients before treatment for the APTT test was 22.4±0.89 (comparable with the Patient Control Group value of 25.2±1.37) and was significantly different from the clinically healthy group value of 49.1±7. After treatment the patients had a mean value of 46.9±6.45 and was therefore within the 'normal range' of clotting times i.e. had been normalized.

The average value for patients before treatment for the PT test was 13.5±0.94 (comparable with the Patient Control Group value of 17.3±4.05) and lower than the clinically healthy group value of 23.7±4.01. After treatment the patients had a mean value of 25.3±4.05 and was therefore within the 'normal range' of clotting times i.e. had been normalized.

The average value for patients before treatment for the SCT test was 151±15.0 (comparable with the Patient Control Group value of 137±11.5) and significantly lower than the clinically healthy group value of 248±10.0. After treatment the patients had a mean value of 235±17.9 and was therefore within the 'normal range' of clotting times i.e. had been normalized.

The average value for patients before treatment for the KCT test was 51.2±4.59 (comparable with the Patient Control Group value of 50.3±2.16) and was significantly different from the clinically healthy group mean value of 133±23.7. After treatment the patients had a mean value of 126±34.2 and was therefore within the 'normal range' of clotting times i.e. had been normalized.

These results show that anti-abzyme therapy can be used to normalize clotting times (using all Internationally recognized clotting time assays) and reduce the risk of thrombosis and hence heart attack and stroke.

TABLE 1

| IgG from human atherosclerotic lesion, in µg | Lipid peroxidation, in µM MDA per ml | |
|---|---|---|
| | + 10 µl ovine Chlamydia | + 2.5 µl feline Chlamydia |
| 0 (control) | 3 ± 0.4 | 0 ± 0.3 |
| 0.18 | 6 ± 1.1 | 2 ± 0.7 |
| 0.36 | 2 ± 1.2 | 0 ± 0.5 |
| 0.57 | 10 ± 0.9 | 1 ± 0.2 |

TABLE 1-continued

| IgG from human atherosclerotic lesion, in µg | Lipid peroxidation, in µM MDA per ml | |
|---|---|---|
| | + 10 µl ovine Chlamydia | + 2.5 µl feline Chlamydia |
| 0.8 | 18 ± 1.0 | 0 ± 0.4 |
| 1.35 | 19 ± 0.7 | 0 ± 0.5 |
| 1.8 | 26 ± 1.3 | 0 ± 0.8 |
| 5.4 | | 4 ± 0.3 |
| 8.0 | | 23 ± 1.5 |

TABLE 2

| Tested systems | Lipid peroxidation in serum, in µM MDA/ml | |
|---|---|---|
| | without Chlamydia | + 10 µl ovine Chlamydia |
| Lipoproteins + antibodies (1st control) | | |
| Serum lipoproteins + 1 µg/ml of lesion IgG* | 130 ± 9.43 | 193 ± 19.9 |
| Only antibodies (2nd control) | 246 ± 17.5 | 342 ± 8.52 |
| Lipoprotein removed from serum by ultracentrifugation + 1 µg/ml lesion IgG* Removal of antibodies by preabsorption with serum lipoproteins | 29 ± 3.57 | 63 ± 5.42 |
| Serum was initially incubated with 1 µg/ml of lesion IgG* and then lipoproteins were removed by ultracentrifugation | 35 ± 4.66 | 23 ± 1.71 |

TABLE 3

| Serum | Control serum, MDA in µM/ml | Patient No3' serum, MDA in µM/ml |
|---|---|---|
| Initial level | 58 ± 4.5 | 187 ± 5.0 (100%) |
| +6.25 µl feline Chlamydia | 50 ± 2.8 | 225 ± 9.9 (120%) $p < 0.05$ |

TABLE 4

| Samples | Control' serum, MDA in µM/ml | | | Patient No2' serum, MDA in µM/ml | | |
|---|---|---|---|---|---|---|
| | Initial level | + ovine Chlamydia 10 µl | 100 µl | Initial level | + ovine Chlamydia 10 µl | 100 µl |
| Serum | 56 ± 6.4 | 58 ± 5.0 | 48 ± 6.6 | 128 ± 9.0 (100%) | 202 ± 13.4 (158%) $p < 0.01$ | 580 ± 24.2 (453%) $p < 0.001$ |
| Serum-IgG | 52 ± 6.2 | 60 ± 6.6 | 62 ± 7.2 | 76 ± 4.4 | 72 ± 6.8 | 96 ± 8.4 |

TABLE 5

| Cases | Lipid peroxidation in µM MDA per 1 ml of serum | | |
|---|---|---|---|
| | Before the addition of Chlamydia* | After the addition of Chlamydia* | Inrement |
| Control: K | 58 | 98 | 32 |
| K1 | 104 | 124 | 20 |
| K2 | 124 | 148 | 24 |
| K3 | 131 | 168 | 37 |
| K4 | 106 | 124 | 18 |
| M | 112 | 108 | -4/0 |
| M1 | 70 (1/10 or 10%) | 70 (1/10 or 10%) | 0 |
| M2 | 78 | 86 | 8 |
| M3 | 102 | 80 | -22/0 |
| M4 | 84 | 76 | -8/0 |
| | $96.8 \pm 3.99$ (n = 10) | $108 \pm 5.73$ (n = 10) $p_{(+Chlamydia)} > 0.05$ | $13.9 \pm 5.14$ (n = 10) |
| Patients: 1 | 116 | 166 | 50 |
| 4 | 86 | 106 | 20 |
| 5 | 122 | 168 | 46 |
| 6 | 40 | 62 | 22 |
| 6a | 208 | 336 | 128 |
| 7 | 118 | 166 | 48 |
| 8 | 82 | 98 | 16 |
| 9 | 160 | 290 | 130 |
| 10 | 60 | 80 | 20 |
| 11 | 236 | 368 | 132 |
| 12 | 256 | 328 | 72 |
| 13 | 174 | 350 | 176 |
| 14 | 168 | 306 | 138 |
| 15 | 126 | 162 | 36 |
| 16 | 290 | 290 | 0 |
| 17 | 246 | 342 | 96 |
| 18 | 270 (13/21 or 62%) | 376 (17/21 or 81%) | 106 |
| 19 | 156 | 272 | 116 |
| 20 | 164 | 312 | 148 |
| 21 | 206 | 344 | 138 |
| 22 | 290 | 332 | 42 |
| | $170 \pm 10.8$ (n = 21) $p_{(control)} < 0.001$ | $250 \pm 15.0$ (n = 21) $p_{(control)} < 0.001$ $p_{(+Chlamydia)} < 0.01$ | $80.0 \pm 13.1$ (n = 21) $p_{(control)} < 0.001$ |

TABLE 6

| LDL, 480 µg of protein | Level of MDA production by 0.82 µg of lesion IgG, in µM |
|---|---|
| Control | $0.49 \pm 0.023$ |
| +0.1 M sodium formate | 0 |
| +0.1 mM ascorbic acid* | 0 |
| +0.1 M benzoic acid | 0 |
| +1% DMSO* | 0 |

*Antioxidants approved by for use in humans in most developed countries.

TABLE 7

| Metals | Chelators | Proprietary Preparations |
|---|---|---|
| $Fe^{+2}/Fe^{+3}$ | Desferrioxamine Mesylate | Canad.: Zinecard; Fr.: Cardioxane; Ital.: Cardioxane; Eucardion; USA: Zinecard. |
| | Haem Derivatives | Austral.: Panhematin; Fr.: Normosang; USA: Panhematin. |
| $Cu^{+1}/Cu^{+2}$ | Penicillamine | Aust.: Artamin; Distamine; Austral.: D-Penamine; Belg.: Kelatin; Canad.: Cuprimine; Depen; Fr.: Trolovol; Ger.: Metacaptase; Trisorcin; Trolovol; Irl.: Distamine; Ital.: Pemine; Sufortan; Neth.: Cuprimine, Distamine; Gerodyl; Kelatin; Norw.: Cuprimine; S. Afr.: Metalcaptase; Spain: Cuprein; |

TABLE 7-continued

| Metals | Chelators | Proprietary Preparations |
|---|---|---|
| | Tiopronin | Sufortanon; Swed.: Cuprimine; Switz.: Mercaptyl; UK: Distamine, Pendramine; USA: Cuprimine; Depen. Fr.: Acadione; Ger.: Captimer; Ital.: Epatiol; Mucolysin; Mucosyt; Thiola; Tioglis; Spain: Sutilan; Switz.: Mucolysin; USA: Thiola. Multi-ingredient: Ital.: Mucolysin Antibiotico; Spain: Hepadigest. |
| | Trientine Dihydrochloride | USA: Syprine. |
| | Diethyldithio-carbamate | |
| | Acetyl-salicylic acid | |
| $Me^{+2}$* | Disodium/ Trisodium Edetate | Fr.: Chelatran; Tracemate; Irl.: Limclair; UK: Limclair; USA: Disotate; Endrate. Multi-ingredient: Canad.: Murine Supplement Tears; Fr.: Vitaclair; Ger.: Complete; Duracare; Oxysept; UK: Uriflex G; Uriflex R. |
| | Edetic Acid | Multi-ingredient: Ital.: Conta-Lens Wetting; USA: Summer's Eve Post-Menstrual; Triv; Vagisec Plus; Zonite. |
| | Unithiol | Ger.: Dimaval; Mercuval. |
| Other metals of transient valence | | |

*Any bivalent metal

TABLE 8

| Antibacterial agents | Proprietary Preparations |
|---|---|
| Tetracycline | Aust: Achromycin; Actisite; Hostacyclin; Latycin; Steclin; tetrarco; Austral.: Achromycin; Achromycin V; Latycin; Mysteclin; Panmycin P; Steclin-V; Tetramykoin; Tetrex; Belg.: Hostacucline; Canad.: Achromycin; Achromycin V; Apo-Tetra; Novo-Tetra; Nu-Tetra; Tetracyn; Fr.: Florocycline; Hexacycline; Tetramig; Ger.: Achromycin; Akne-Pyodron Kur; Akne-Pyodron oral; Dispatetrin; Hostacyclin; Imex; Quimocyclin N; Sagittacin N; Steclin; Supramycin; Tefilin; Tetrabakat; Tetrablet; Tetracitro S; Tetralution; Ital.: Acromicina; Ambramicina; Calociclina; Ibicyn; Spaciclina; Tetra-Proter; Tetrabioptal; Tetrafosammina; Neth.: Tetrarco; S.Afr.: Achromycin; Arcanacycline; Gammatet; Hostacycline; Rotet; Tetrex; Spain: Actisite; Ambramicia; Britaciclina; Kinciclina; Quimpe Antibiotico; Tetra Hubber; Tetralen; Tetrarco Simple; Swed.: Achromycin; Actisite; Switz.: Achromycine; Actisite; Servitet; Tetraseptine; Triphacycline; UK: Achromycin; Economycin; Sustamycin; Tetrabid-Organon; Tetrachel; USA: Achromycin V; Achromycin; Actisite; Nor-Tet; Panmycin; Robitet Robicaps; Sumycin; Teline; Tetracap; Tetralan; Tetram.* |
| Erythromycin | |
| Azithromycin | |
| Roxithromycin | |
| Ofloxacin | |
| Clinafloxacin | |
| Ciprofloxacin | |
| Clindamycin | |
| Doxycycline | |
| Minocycline | |

*Multi-ingredient: numerous preparations

TABLE 9

| Antioxidants | Proprietary Preparations: |
|---|---|
| Alpha-Tocopherol | Aust.: Avigilen; Ephynal; Etocovit; Evit; Evitol; Tetefit Vitamin E; Austral: Alpha Keri Silky Smooth; Bioglan Micelle E; Bioglan Natural E; Bioglan Water Soluble E; Chew-E; Da1-E; Invite E Forte; Invite E; Marco E; Mega E; Megavit Natural E; Belg.: Ephynal; Canad.: Aquasol E; Novo E; Organex; Vita-E; Fr.: Ephynal; Tocalfa; Toco; Tocomine; Ger.: Antioxidants E; Biopto-E; Detulin; E-Muslin; E-Vicotrat; Ecoro; Embial; Ephynal; Pexan E; Puncto E; Sanavitan S; Tocorell; Tocovenos; Tocovital; Togasan; Vitagutt Vitamin E; Irl.: Ephynal; Ital.: E Perle; E-Vit; E-Vitum; Ephynal; Evasen Cream; Evion; Evitina; Fertilvit; Na-To-Caps; Tocoferina E; Tocoferolo Bioglan; Tocogen; Viteril; Norw.: AFI-E; Ido-E; S. Afr.: Ephynal; Spain: Auxina E; Ephynal; Glutaneurina B6 Fte; Swed.: Ephynal; Opto Vit-E; Vitacim; UK: Bio E; Ephynal; Praire Gold; Vita-E; USA: Amino-Opti-E; Aquasol E; Aquavit-E; Vita-Plus E; Vitec.* |
| Mannitol | Aust.: Osmofundin 20%; Austral.: Mede-Prep; Osmitrol; Canad.: Osmitrol; Fr.: Manicol; Ger.: Eufusol M 20; Mannit-Losung; Osmofundin 15%; Osmosteril 20%; Thomaemannit; Ital.: Isotol; Mannistol; Switz.: Mannite; USA: Osmitrol; Resectisol.* |
| Silidianin | Aust.: Apihepar.; Biogelat leberschutz; Hepar Pasc Mono; Legalon; Silyhexal; Austral.: Herbal Liver Formula; Liver Tonic Capsules; Prol.; Belg.: Legalon SIL; Fr.: Legalon; Ger.: Alepa; Ardeyhepan N; Carduus-monoplant; Cefasliymarin; Divinal-Hepa; Durasilymarin; Hegrimarin; Heliplant; Hepa-loges N; Hepa-Merz Sil; Hepar-Pasc; Heparano N; Heparsyx N; Hepatorell; Hepatos; Heplant; Legalon; Legalon SIL; Logomed Leber-Kapseln; Mariendistel Curarina; Phytohepar; Poikicholan; Probiophyt V; Silibene; Silicur; Silimarit; Silmar; Sulfolitruw H., Vit-o-Mar; Ital: Eparsil; Legalon; Locasil; Marsil; Silepar; Silimarin; Silirex; Silliver; Silmar; Trissil; S.Afr.: Legalon; Spain: Legalon; Silarine; Silimazu; Switz.: Legalon; Legalon SIL. |
| Ascorbic acid | |
| Etc. | |

*Multi-ingredient: numerous preparations

TABLE 10

| Sheep | Lipid peroxidation of sheep sera in μM MDA per ml | |
|---|---|---|
| | − Chlamydia | + Chlamydia |
| Pre-vaccinated | | |
| No. 1 | 44 | 39 (89%) |
| No. 2 | 59 | 67 (114%) |
| Post-vaccinated | | |
| No. 8 | 67 | 85 (127%) |
| No. 5 | 54 | 46 (85%) |
| Post-abortion (wild type) | | |
| A | 48 | 102 (212%) |
| B | 63 | 118 (187%) |

TABLE 11

| $Me^{2+}$-binding agent, 10 μM of each | Lipid oxidising activity of anti-Chlamydia abzymes in, μM MDA/ml* | Result | Potential clinical use of agent for inhibition of anti-Chlamydia abzymes |
|---|---|---|---|
| Control | 24.3 | | |
| $NaN_3$ | 0 | Positive | Highly toxic, no use |
| KCN | 0 | Positive | Highly toxic, no use |
| Tetracycline | 18.3 | Negative | No use |
| DTPA | 45.2 | Negative | No use |
| Picolinic acid | 0 | Positive | Prooxidant, no use |
| $Cu^{2+}$-chelators | | | |
| DDC | 0 | Positive | Possible use ("Imutiol") |
| Acetylsalicylic acid | 6.2 | Positive | Possible use ("Aspirin") |
| Penicillamine | 0 | Positive | Possible use ("Penicillamine") |

*Each number is a mean of duplicate/triplicate measurement, and calculated as a difference between the level of MDA accumulation in the tested serum before and after the addition of 0.5 of immunisation dose of ovine Chlamydia vaccine ('Intervet').

TABLE 12

| Inhibitor | Mechanism of action | In-vitro Inhibition (+ = inhibition) (− = no inhibition) |
|---|---|---|
| Tetracycline | Fe2+ inhibition | − |
| DDC | Free and bound Cu2+ inhibition | + |
| Aspirin (acetylsalicylic acid) | Free and bound Cu2+ inhibition | + |
| Penicillamine | Free and bound Cu2+ inhibition | + |
| CN— | Free and bound Metal inhibition | + |
| N3 | Free and bound Metal inhibition | + |
| DTPA | Free metal inhibition only | − |
| Picolinic acid | Free and bound Metal inhibition | + |

TABLE 13

| Initial of patient with CHD | Level of activity of anti-Chlamydia abzymes in μM MDA/ml | |
|---|---|---|
| | Before taking aspirin | 7 days after starting to take 250 mg of aspirin daily |
| S | 45 | 0 |
| A | 100 | 20 |
| Y | 45 | 0 |

TABLE 14

Level of activity of anti-Chlamydia abzymes in μM MDA/ml

| Initial of patient | Aspirin intake 250 mg daily | After stopping taking aspirin for 7 days | 7 days after re-starting to take 250 mg aspirin daily |
|---|---|---|---|
| F | 10 | 65 | 20 |

TABLE 15

Anti-Chlamydia abzyme activity, in μM MDA/ml

| Patient | before treatment | 15 days after the start of the treatment | 30 days after the start of the treatmnet |
|---|---|---|---|
| 1. | 30 | 6.7 | 3.3 |
| 2. | 90 | 6.7 | — |
| 3. | 80 | 0 | 0 |
| 4. | 40 | 60 | 37 |
| 5. | 50 | 0 | 0 |
| 6. | 15 | 8.3 | 28 |
| 7. | 10 | 6.7 | 3.3 |
| 8. | 35 | 33 | 10 |
| 9. | 85 | 75 | 78 |
| 10. | 30 | 0 | 0 |
| 11. | 40 | — | — |
|  | 45.9 | 19.6 | 17.7 |

TABLE 16

Anti-Chlamydia abzyme activity, in μM MDA/ml

| Patient | before treatment | 15 days after the start of the treatment |
|---|---|---|
| 12 | 100 | 43 |
| 13 | 93 | 27 |
| 14 | 33 | 0 |
| 15 | 30 | 0 |
| 16 | 153 | 0 |
| 17 | 15 | 0 |
| 18 | 25 | 3.3 |
| 19 | 15 | 0 |
|  | 58.0 | 9.16 |

TABLE 17

| Patient | Clinical condition Before treatment | After 15 days of treatment |
|---|---|---|
| 2 | Unstable angina; ECG exercise test was inapplicable | Stable condition; ECG exercise test demonstrated a significant tolerance; angina attacks were not recorded for this period; return to his job in full capacity |
| 5 | Classified as angina class III; 10 tablets of nitroglycerine daily | Based on the improvement of ECG exercise test, patient condition was reclassified as angina class II; reduction in the frequency and severity of angina attacks; 5 tablets of nitroglycerine daily; |

TABLE 18

|  |  |  |  |  | MYOCARDIAL INFARCTION | |
|---|---|---|---|---|---|---|
| CONTROL | SILENT ISCHAEMIA | STABLE ANGINA | UNSTABLE ANGINA | Acute Phase 1st-3rd Day | 14th Day |
| 6.36 ± 1.14 (n = 67) | 68.8 ± 16.7 (n = 15) | 37.1 ± 2.23 (n = 193) | 101 ± 18.1 (n = 13) | 14.4 ± 2.60 (n = 25) | 80.6 ± 21.4 (n = 14) |
| 11/67 = 16% | 14/15 = 93% | 130/193 = 67% | 12/13 = 92% | 12/25 = 48% | 12/14 = 86% |
|  | $p_{control}$ < 0.001 | $p_{control}$ < 0.001 | $p_{control}$ < 0.001 | $p_{control}$ < 0.01 | $p_{acute\,phase}$ < 0.01 |
|  |  |  | $p_{stable\,angina}$ < 0.001 | $p_{unstable\,angina}$ < 0.001 |  |

TABLE 19

ISCHAEMIC HEART DISEASE (total): 168/235 = 71%

| STABLE ANGINA | | | | | | UNSTABLE ANGINA | |
|---|---|---|---|---|---|---|---|
| I | | II | | III | | IV | |
|  | + aspirin |  | + aspirin |  | + aspirin |  | + aspirin |
| 15 | 0 | 45 | 30 | 45 | 20 | 70 | 180 |
| 75 | 5 | 0 | 5 | 40 | 0 | 90 | 130 |
| 15 | 45 | 70 | 10 | 10 | 45 | 30 | 70 |
| 15 | 0 | 50 | 10 | 45 | 0 | 250 | 0 |
|  | 10 | 20 | 0 | 60 | 5 | 140 | 37 |
|  | 0 | 0 | 5 | 90 | 35 | 130 | 90 |
|  |  | 8 | 25 | 25 | 0 |  | 100 |

TABLE 19-continued

ISCHAEMIC HEART DISEASE (total): 168/235 = 71%

| STABLE ANGINA | | | UNSTABLE ANGINA |
|---|---|---|---|
| I | II | III | IV |
| + aspirin | + aspirin | + aspirin | + aspirin |

| I | | II | | III | | IV | |
|---|---|---|---|---|---|---|---|
| | | 0 | 0 | 30 | 15 | | |
| | | 53 | 5 | 153 | 30 | | |
| | | 18 | 22.5 | 15 | 105 | | |
| | | 17 | 0 | 93.3 | | | |
| | | 43 | 5 | | | | |
| | | 10 | 3.3 | | | | |
| | | 50 | 0 | | | | |
| | | 32.5 | 16.7 | | | | |
| | | 100 | | | | | |
| | 1/6 | | 4/15 | | 6/10 | | 6/7 |
| | 17% | | 27% | | 60% | | 86% |
| 30.0 | 10.0 | 32.2 | 9.2 | 56.0 | 25.5 | 119 | 86.7 |
| (n = 4) | (n = 6) | (n = 16) | (n = 15) | (n = 11) | (n = 10) | (n = 6) | (n = 7) |
| 4/9 = 44% | | 12/26 = 46% | | 12/17 = 71% | | 12/13 = 92% | |

TABLE 20

| | Anti-Chlamydia IgG, ELISA** Day of the infection | | Anti-Chlamydia abzymes, in µM MDA/ml** Day of the infection | |
|---|---|---|---|---|
| Rabbit | 0 | 14 | 0 | 14 |
| 1 | 0 | 1:1,600 | 0 | 71 |
| 2 | 0 | 1:3,200 | — | 203 |
| 3 | 0 | 1:800 | 0 | 131 |
| Control | 0 | 0 | 0 | 0 |

TABLE 21

| | Anti-Chlamydia IgG, ELISA** Day of the infection | | | Anti-Chlamydia abzymes, in µM MDA/ml** Day of the infection | | |
|---|---|---|---|---|---|---|
| | | | 22 | | | 22 |
| Rabbit | 0 | 14 | § + vaccine | 0 | 14 | § + vaccine |
| 1 | 0 | 1:1,600 | 1:1,600 | — | 71 | 165 |
| 2 | 0 | 1:3,200 | 1:3,200 | — | — | 203 | 180 |
| 3 | 0 | 1:800 | — | 1:1,600 | 0 | 131 | — | 64 |
| Control | 0 | 0 | — | — | 0 | 0 | — | — |

TABLE 22

Anti-Chlamydia abzyme activity, in µM MDA/ml

| Patients in Therapy Group A | before treatment | 15 days after the start of treatment | 30 days after the start of treatment | 45 days after the start of treatment | 60 days after the start of treatment |
|---|---|---|---|---|---|
| TGA1 | 30 | 6.7 | 3.3 | 0 | 0 |
| TGA2 | 90 | 6.7 | 78** | 17 | 3.3 |
| TGA3 | 80 | 0 | 0 | 0 | 6.7 |
| TGA4 | 40 | 60* | 37* | 0 | 0 |
| TGA5 | 50 | 0 | 0 | 20* | 0 |
| TGA6 | 15 | 8.3 | 28** | 43* | 6.7 |
| TGA7 | 28 | 6.7 | 3.3 | 3.3 | 0 |
| TGA8 | 35 | 33 | 10 | 3.3 | 0.5 |

TABLE 22-continued

Anti-Chlamydia abzyme activity, in µM MDA/ml

| Patients in Therapy Group A | before treatment | 15 days after the start of treatment | 30 days after the start of treatment | 45 days after the start of treatment | 60 days after the start of treatment |
|---|---|---|---|---|---|
| TGA9 | 85 | 75* | 78* | 0 | 0 |
| TGA10 | 30 | 0 | 0 | 5.0 | 0 |
| TGA11 | 40 | 52* | 10 | 0 | 0 |
| | 47.5 | 22.5 | 22.5 | 7.4 | 1.6 |

TABLE 23

Anti-Chlamydia abzyme activity, in µM MDA/ml

| Patients in Therapy Group B | before treatment | 15 days after the start of treatment | 30 days after the start of treatment | 45 days after the start of treatment | 60 days after the start of treatment |
|---|---|---|---|---|---|
| TGB1 | 100 | 43 | 10 | 0 | — |
| TGB2 | 93 | 27 | 30 | 0 | 10 |
| TGB3 | 33 | 0 | 0 | 0 | 0 |
| TGB4 | 30 | 0 | 6.7 | 0 | 3.3 |
| TGB5 | 153 | 0 | 0 | 0 | 3.3 |
| TGB6 | 15 | 0 | 0 | 3.3 | 0 |
| TGB7 | 25 | 3.3 | 0 | 80** | 0 |
| TGB8 | 15 | 0 | 3.3 | 10 | 0 |
| | 58.0 | 9.16 | 6.25 | 11.6 | 2.4 |

TABLE 24

Anti-Chlamydia abzyme activity, in µM MDA/ml

| Patients in Therapy Group C | before treatment | 15 days after the start of treatment | 30 days after the start of treatment | 45 days after the start of treatment |
|---|---|---|---|---|
| TGC1 | 15 | 28* | 23* | 23* |
| TGC2 | 23 | 0 | 0 | 0 |
| TGC3 | 25 | 17 | 0 | 13 |
| TGC4 | 60 | 0 | 0 | 0 |

TABLE 24-continued

| Patients in Therapy Group C | Anti-Chlamydia abzyme activity, in µM MDA/ml | | | |
|---|---|---|---|---|
| | before treatment | 15 days after the start of treatment | 30 days after the start of treatment | 45 days after the start of treatment |
| TGC5 | 45 | 1.7 | 0 | 0 |
| TGC6 | 43 | 18 | 0 | 0 |
| TGC7 | 140 | 53 | 20 | 20 |
| TGC8 | 130 | 57 | 17 | 3.3 |
| TGC9 | 18 | 0 | 0 | 13 |
| | 55.6 | 19.4 | 6.67 | 8.10 |

TABLE 25

| Patients in Therapy Group D | Anti-Chlamydia abzyme activity, in µM MDA/ml | |
|---|---|---|
| | before treatment | 60 days after the start of treatment |
| TGD1 | 103 | 63 |
| TGD2 | 253 | 103 |
| | 178 | 83.2 |

TABLE 26

| Patient Control Group (PCG) | Anti-Chlamydia abzyme activity, in µM MDA/ml | |
|---|---|---|
| | At Day 1 | At Day 60 |
| PCG1 | 43 | 43 |
| PCG2 | 93 | 70 |
| PCG3 | 60 | 53 |
| PCG4 | 17 | 25 |
| PCG5 | 70 | 55 |
| PCG6 | 25 | 23 |
| PCG7 | 20 | 34 |
| PCG8 | 70 | 68 |
| PCG9 | 20 | 20 |
| PCG10 | 30 | 27 |
| PCG11 | 20 | 45 |
| PCG12 | 170 | 150 |
| PCG13 | 70 | 103 |
| PCG14 | 45 | 57 |
| PCG15 | 50 | 55 |
| PCG16 | 53 | 71 |
| PCG17 | 18 | 45 |
| PCG18 | 15 | 34 |
| PCG19 | 45 | 67 |
| PCG20 | 60 | 61 |
| | 50.0 ± 7.08 | 55.3 ± 6.18 |

TABLE 27

| Parameter | | Azithromycin Therapy Group A | Azithromycin + antioxidants Therapy Group C | Azithromycin + aspirin Therapy Group B | PCG | Norm |
|---|---|---|---|---|---|---|
| Anti-Chlamydia abzymes activity, in µM/MDA/ml | Before treatment | 47.5 ± 8.96 | 55.0 ± 16.2 | 58.0 ± 20.4 | 50.0 ± 7.08 | 6.36 ± 1.14 |
| | 60 days after treatment | 1.6 ± 0.89 $p < 0.001$* | 8.1 ± 3.60 $p < 0.05$* | 2.4 ± 1.37 $p < 0.05$* | 55.3 ± 6.18 $p > 0.05$ | |
| Anti-Chlamydia IgG§, (titers)$^{-1}$ | Before treatment | 43.6 | 48.5 | 52.0 | — | 0 |
| | 60 days after treatment | 0 $p < 0.001$* | 0 $p < 0.001$* | 0 $p < 0.001$* | — | 0 |
| Clinical Status modified Rose G., Blackburn H. Questionnaire | Before treatment | 19.4 ± 1.79 | 18.6 ± 0.81 | 20.4 ± 1.79 | 19.8 ± 1.43 | 0 |
| | 60 days after treatment | 14.4 ± 1.14 $p < 0.05$* | 15.4 ± 1.75 $p > 0.05$ | 15.0 ± 1.17 $p < 0.01$* | 21.5 ± 1.19 | |
| Coagulation Silica Clotting Time**, in sec | Before treatment | | 151 ± 18.8 | | | 200-250 |
| | 60 days after treatment | | 222 ± 18.4 $p < 0.05$* | | | |

TABLE 28

| Therapy Group/Patient | Score by modified Rose-Blackburn Questionnaire | |
|---|---|---|
| | Before treatment | 60 days after start of the treatment |
| Therapy Group A | | |
| TGA1 | 25 | 17 |
| TGA2 | 22 | 19 |
| TGA3 | 12 | 10 |

TABLE 28-continued

| Therapy Group/Patient | Score by modified Rose-Blackburn Questionnaire | |
|---|---|---|
| | Before treatment | 60 days after start of the treatment |
| TGA4 | 19 | 13 |
| TGA5 | 23 | 16 |
| TGA6 | 21 | 18 |
| TGA7 | 25 | 15 |
| TGA8 | 16 | 15 |
| TGA9 | 10 | 8 |
| TGA10 | 15 | 11 |
| TGA11 | 25 | 17 |
| | 19.4 ± 1.79 | 14.4 ± 1.14 |
| Therapy Group B | | |
| TGB1 | 21 | 19 |
| TGB2 | 17 | 14 |
| TGB3 | 23 | 14 |
| TGB4 | 24 | 12 |
| TGB5 | 19 | 19 |
| TGB6 | 16 | - |
| TGB7 | 24 | 13 |
| TGB8 | 19 | 14 |
| | 20.4 ± 1.24 | 15.0 ± 1.17 |
| Therapy Group C | | |
| TGC1 | 15 | 9 |
| TGC2 | 21 | 21 |
| TGC3 | 18 | 13 |
| TGC4 | 16 | 16 |
| TGC5 | 19 | 9 |
| TGC6 | 21 | 21 |
| TGC7 | 17 | 17 |
| TGC8 | 20 | 13 |
| TGC9 | 20 | 20 |
| | 18.6 ± 0.81 | 15.4 ± 1.75 |

TABLE 29

| Patient code | Abzyme activity Day 0 | Abzyme activity Day 60 | Rose Blackthorn Score Day 0 | Rose Blackthorn Score Day 60 |
|---|---|---|---|---|
| TGA2 | 90 | 3.3 | 22 | 19 |
| TGA3 | 80 | 6.7 | 12 | 10 |
| TGA4 | 40 | 0 | 19 | 13 |
| TGA6 | 15 | 6.7 | 21 | 18 |
| TGB3 | 15 | 0 | 23 | 14 |
| TGC5 | 45 | 0 | 19 | 9 |
| TGC7 | 140 | 20 | 17 | 17 |

TABLE 30

| Compound and its concentration | Lipid oxidising activity of anti-Chlamydia abzymes in, μM MDA/ml* | Comments |
|---|---|---|
| Control | 61 | |
| Azithromycin** | | |
| Suspension in water | | Antioxidant properties are |
| 20 μM | 0 | comparable with |
| 10 μM | 0 | or stronger than |

TABLE 30-continued

| Compound and its concentration | Lipid oxidising activity of anti-Chlamydia abzymes in, μM MDA/ml* | Comments |
|---|---|---|
| 2 μM | 0 | α-Tocopherol |
| 1 μM | 19 | |
| Suspension in DMSO | | |
| 5 μM | 0 | |
| 1 μM | 7 | |
| α-Tocopherol in DMSO | | |
| 10 μM | 0 | |
| 1 μM | 15 | |

TABLE 31

| DRUGS | Anti-Abzyme activity, in μM MDA/ml |
|---|---|
| Control | 21.7 |
| Beta Blocker | |
| 1. Propranolol Hydrochloride OBSIDAN | |
| 175 μM | 21.3 |
| 35 μM | 18.3 |
| Nitrates | |
| 1. Glyceryl Trinitrate PERLINGANIT | |
| 220 μM | 0 |
| 44 μM | 0 |
| 22 μM | 0 |
| 4.4 μM | 0 |
| 2. Isosorbide Dinitrate ISOKET | |
| 211 μM | 0 |
| 42 μM | 0 |
| Magnesium | |
| 1. Magnesium Sulfate | |
| 101 μM | 0 |
| 51 μM | 0 |
| 40 μM | 16 |
| 20 μM | 26 |
| Heparin | |
| 1. Heparin | |
| 0.1 mg/ml | 19.7 |
| 2. Nadroparin Calcium FRAXIPARINE | |
| 465 UI | 12.8 |
| 95 UI | 20.5 |
| Calcium-Channel Blocker | |
| 1. Verapamil Hydrochloride ISOPTIN | |
| 51 μM | 3 |
| 10.2 μM | 24.0 |
| 5.1 μM | 21.5 |
| Corticosteroids | |
| 1. Dexamethasone | |
| 25 μM | 24.5 |
| 12.5 μM | 20.1 |
| Antibiotics | |
| 1. Lincomycin Hydrochloride | |
| 13 μM | 30.3 |
| 6.5 μM | 28.5 |

TABLE 32

| | | Abbreviation for clotting time measurements | Means of results from patient therapy groups A, B, C and D groups | Abbreviation for clotting time measurements | Not treated Patient Control Group (PCG) | Our Clinically Healthy Control Group |
|---|---|---|---|---|---|---|
| Coagulation* | Before treatment | APTT | 22.4 ± 0.89 | | | |
| | | PT | 13.5 ± 0.94 | | | |
| | | SCT | 151 ± 15.0 | APTT | 25.2 ± 1.37 | 49.1 ± 7.00 |
| | | KCT | 51.2 ± 4.59 | | | |
| | 60 days after treatment | APTT | 46.9 ± 6.45 $p < 0.005$* | PT | 17.3 ± 4.05 | 23.7 ± 4.01 |
| | | PT | 25.3 ± 4.05 $p < 0.05$* | SCT | 137 ± 11.5 | 248 ± 10.0 |
| | | SCT | 235 ± 17.9 $p < 0.005$* | KCT | 50.3 ± 2.16 | 133 ± 23.7 |
| | | KCT | 126 ± 34.2 $p > 0.05$ | | | |

What is claimed is:

1. A method of screening for a test compound which may be useful in the treatment of an atherosclerotic disorder comprising:
   (a) contacting a first portion of a sample obtained from an individual having an atherosclerotic disorder with *Chlamydia* cells selected from the group consisting of *C. pneumoniae* and *C. psittaci* in the presence of the test compound to produce a sample (a),
   (b) contacting a second portion of the sample obtained from the individual having an atherosclerotic disorder with *Chlamydia* cells selected from the group consisting of *C. pneumoniae* and *C. psittaci* in the absence of the test compound to produce a sample (b),
   wherein said sample is an atherosclerotic lesion or serum sample comprising IgG molecules which bind to said *Chlamydia* cells and have lipid oxidation activity, and
   wherein said test compound is a potential inhibitor of antibody-mediated lipid oxidation; and
   (c) measuring lipid oxidation in sample (a) and lipid oxidation in sample (b) and comparing the lipid oxidation in sample (a) and the lipid oxidation in sample (b),
   wherein when the lipid oxidation in sample (a) is less than the lipid oxidation in sample (b), then the test compound may be useful in the treatment of an atherosclerotic disorder.

2. The method according to claim 1 wherein said measuring comprises determining the production of a lipid oxidation product.

3. The method according to claim 2 wherein the lipid oxidation product is malondialdehyde (MDA).

4. A method for screening for a test compound which may be useful in the treatment of an atherosclerotic disorder comprising:
   (a) admixing (1) a first portion of a sample comprising IgG molecules which bind to *Chlamydia* cells selected from the group consisting of *C. pneumoniae* and *C. psittaci*, and which have lipid oxidation activity, (2) *Chlamydia* cells selected from the group consisting of *C. pneumoniae* and *C. psittaci*, and (3) the test compound, to produce a sample (a);
   (b) admixing a second portion of the sample with *Chlamydia* cells selected from the group consisting of *C. pneumoniae* and *C. psittaci* in the absence of the test compound to produce a sample (b), and
   (c) determining the lipid oxidation in sample (a) and lipid oxidation in sample (b) and comparing the lipid oxidation in sample (a) and the lipid oxidation in sample (b),
   wherein when the lipid oxidation in sample (a) is less than the lipid oxidation in sample (b), then the test compound may be useful in the treatment of an atherosclerotic disorder.

5. The method according to claim 4 wherein said determining comprises measuring the production of a lipid oxidation product.

6. The method according to claim 5 wherein the lipid oxidation product is malondialdehyde (MDA).

7. A method of screening for a test compound which may be useful in the treatment of an atherosclerotic disorder comprising:
   (a) obtaining a serum sample (a) from an animal comprising IgG molecules which bind to *Chlamydia* cells selected from the group consisting of *C. pneumoniae* and *C. psittaci*, and which have lipid oxidation activity, said animal not having been exposed to the test compound
   (b) introducing the test compound into the vascular system of said animal to produce a tested animal and obtaining a serum sample (b) from said tested animal; and
   (c) determining the serum lipid oxidation activity of sample (a) and the serum lipid oxidation activity of sample (b) and comparing the serum lipid oxidation level of sample (a) and the serum lipid oxidation level of sample (b), wherein when the serum lipid oxidation level of sample (b) is less than the serum lipid oxidation level of sample (a) then the test compound may be useful in the treatment of an atherosclerotic disorder.

8. The method according to claim 7 wherein said determining comprises measuring the production of a lipid oxidation product.

9. The method according to claim 8 wherein the lipid oxidation product is malondialdehyde (MDA).

* * * * *